US008478608B2

(12) United States Patent
Borton et al.

(10) Patent No.: US 8,478,608 B2
(45) Date of Patent: Jul. 2, 2013

(54) SYSTEM AND METHOD TO MEASURE AND MANAGE URGENT CARE REQUESTS

(75) Inventors: Mark C. Borton, Chester, CT (US); Dean Craig Sperry, Windsor, CT (US); Robert Crowell Bausmith, West Hartford, CT (US); David Alan Kirshenbaum, West Hartford, CT (US); Arman Ozgun, New York, NY (US)

(73) Assignee: Equity Health Partners, LLC, Chester, CT (US)

( * ) Notice: Subject to any disclaimer, the term of this patent is extended or adjusted under 35 U.S.C. 154(b) by 226 days.

(21) Appl. No.: 13/154,730

(22) Filed: Jun. 7, 2011

(65) Prior Publication Data
US 2012/0035948 A1    Feb. 9, 2012

Related U.S. Application Data

(60) Provisional application No. 61/352,439, filed on Jun. 8, 2010.

(51) Int. Cl.
*G06Q 10/00* (2012.01)
(52) U.S. Cl.
USPC .................................................. 705/2; 705/3

(58) Field of Classification Search
USPC ............................................................. 705/2, 3
See application file for complete search history.

(56) References Cited

U.S. PATENT DOCUMENTS

| 5,845,254 | A  | * | 12/1998 | Lockwood et al. | 705/2 |
| 7,725,333 | B2 | * | 5/2010  | Dang            | 705/3 |
| 7,991,626 | B2 | * | 8/2011  | Legorreta et al.| 705/2 |
| 7,996,241 | B2 | * | 8/2011  | Zak et al.      | 705/2 |
| 2008/0040151 | A1 | * | 2/2008 | Moore          | 705/2 |

OTHER PUBLICATIONS

Google patents search, Mar. 12, 2013.*

* cited by examiner

*Primary Examiner* — Dilek B Cobanoglu
(74) *Attorney, Agent, or Firm* — Fox Rothschild LLP

(57) ABSTRACT

An innovative tracking software system provides independent proof of primary-care physician (PCP) efforts to improve urgent access to care and coordination of care. PCPs are provided with tools and financial incentives to better manage urgent care requests and thereby provide better service while reducing avoidable hospital utilization (ER and re-admissions) and costs. In particular, independent and accurate measurements of provider performance enable the payment of financial incentives to PCPs.

27 Claims, 42 Drawing Sheets

CareHub

PRIMEHEALTH FAMILY MEDICINE

Elana Lee 05/20/2011 17:00
Settings | Help | Log Out

SEARCH PATIENTS | MANAGE ACCESS | RECONCILE PATIENTS | GET REPORTS

Select a Patient stage:

TO BE ASSESED (4) | TO BE ASSIGNED (4) | TO BE FOLLOWED-UP (4) | DISCHARGES PENDING (0)

TO BE ASSESED

| Time Since Initiated △ | Initiated By | Name (Gender) | Home PCP |
|---|---|---|---|
| 120+ minutes | Discharge | Carbone, Kevin (M) | LeeEl, MD |
| 120+ minutes | ER Followup | Dargie, Zach (M) | IndAr, MD |
| 120+ minutes | PT Req (AH) | Domingo, Dierdre (F) | IndAr, MD |
| 120+ minutes | Discharge | Esposito, Manuela (F) | LeeEl, MD |

—1802

Click on name to get next screen

PRINT SELECTED

⊘ – Opted out of program or no longer using your practice as Home practice
☐ – Belongs to another practice; your practice currently responsible for a Care Event
△ – Identified as having a higher propensity to seek / need urgent care © 2009 Equity Health Partners, LLC.
All rights reserved. Version 0.37.6

FIG. 18B

CareHub

| SEARCH PATIENTS | MANAGE ACCESS | RECONCILE PATIENTS | GET REPORTS |

Elana Lee 05/20/2011 20:50
Settings | Help | Log Out

PATIENT
Kevin Carbone
MRN 884199
2/2/1968 (23)
Level 1
Pt-EL Signed: Yes

Home PCP
Elana Lee, MD
PrimeHealth Family Medicine

PROGRAM
CAFP-First Contact of Care

PROGRAM SPONSOR
Blue Cross Blue Shield of Mars

DISCHARGE STARTED 02/14/2011 13:59 PM          OPEN  [STOP TICKET]

DISCHARGED DATE          02/09/2011
RECEIVED DISCHARGE SUMMARY  [✓]
HOSPITALIZED FOR          UUUUUUUUUUUUUUU
CONTACT INFORMATION

NEW EVENT

ASSESSMENT
PRESENTING FACTORS

WORKING DX

ACCESS TYPE*
[PCP VISIT] [PCP CONSULT] [WALK-IN] [ER] [REFER TO SPECIALIST]
ADDRESS BY*
[ASAP] [TODAY] [TOMORROW AM] [TOMORROW PM] [SET DATE] 05/25/2011

[CANCEL]    [ASSIGN NOW] [ASSIGN LATER]

"We are now back in the 'Assessment' stage of the Tracking module."

FIG. 18C

| Chart Key | ▽ | Top Quintile Range | | Bottom Quintile Range | | Your Performance | | Program Average | | |
|---|---|---|---|---|---|---|---|---|---|---|
| | | Jun 2010 | May 2010 | Apr 2010 | Mar 2010 | Feb 2010 | Jan 2010 | Dec 2008 | Nov 2008 | |
| ☐ PrimeHealth Family Medicine | | | | | | | | | | |
| Top Quintile | | 70 | 84 | 86 | 85 | 80 | 70 | | | |
| | | 84-94 | 86-95 | 87-93 | 87-94 | 87-94 | 85-92 | | | |
| Program Average | | 80 | 81 | 80 | 80 | 76 | 75 | | | |
| Bottom Quintile | | 63-73 | 63-73 | 62-72 | 62-72 | 58-70 | 55-65 | | | |

2320

REPORT PARAMETERS

Report: Urgent Care Requests and Response Time

Date Range:
○ Most Recent 15 Months By Month
○ Most Recent 15 Months By Quarter
⊙ Custom  From: June 2010    To: June 2010

Physician(s): ⊙ Entire Practice
  ☑ Indiri, Ardo MD
  ☑ Kent, Kevin DO
  ☑ Lee, Elana MD Patient(s): ⊙ All Patients
  ○ Level 2 Patients Only Response Time Goal: Access Delivered within [1] Business Days

[UPDATE PARAMETERS]

*Clicking here shows data from which report was generated in next screen*

FIG. 23C

| FCC for Connecticut Medicaid –P4P Measures Category / Measure | Process or Outcome | Data Source | Units | Measured at Level of: | | | | Measurement Frequency | | | | Category Weight & Points |
|---|---|---|---|---|---|---|---|---|---|---|---|---|
| | | | | PCP | Site | FQHC | | Mo | Qtr | Yr | | |
| Access & Continuity | | | Per M/yr | | | | | | | | | 40% |
| Urgent Access: % Urgent Care Requests fulfilled within 2 days by HomePCP or HomePractice or HomeFQHC. | Process | Online tool | 1,150 | | • | | | ☑ | | | | 200 |
| Continuity with Home PCP: % of Urgent Care Requests fulfilled by HomePCP | Process | Online tool | 1,150 | • | | | | ☑ | | | | 100 |
| Continuity with HomePractice: % of Urgent Care Requests fulfilled HomePractice | Process | Online tool | 1,150 | | • | | | ☑ | | | | 75 |
| Continuity with HomeFQHC: % of Urgent Care Requests fulfilled HomeFQHC | Process | Online tool | 1,150 | | | • | | ☑ | | | | 25 |
| Provider & Patient Engagement | | | FCC Total | | | | | | | | | 30% |
| Patient Engagement: % of High-Risk Patient Engagement Letters Signed | Process | Online tool | 1,000 Patients | • | | | | ☑ | | | | 100 |
| Provider Engagement: % of monthly Peer Learning Sessions attended by at least one Practice Site Staff, and at least quarterly by at least one PCP. | Process | FCC Staff | 30-40 PCP 120+ staff | • | • | | | ☑ | | | | 100 |
| Patient Satisfaction: CAHPS survey | Outcome | Phone Survey | 100 x 10+ Sites | | • | | | | | | ☑ | 100 |
| Hospital Utilization | | | Per M/yr | | | | | | | | | 20% |
| Avoidable ER: % of ER visits for Ambulatory Care Sensitive Conditions | Outcome | Claims | ~500 | • | | | | | ☑ | | | 100 |
| Avoidable Admission: % of Admissions for Ambulatory Care Sensitive Conditions | Outcome | Claims | ~20 | • | | | | | ☑ | | | 100 |
| Hospital Discharge Management | | | Per M/yr | | | | | | | | | 10% |
| Post-ER Follow-Up by HomePractice: % of ER visits with HomePractice follow-up (or 3 attempts to contact documented in CareHub) within 7 days of ER visit. | Process | Claims, tool | 1,150 | | • | | | ☑ | | | | 50 |
| Inpatient Discharge Follow-Up by HomePractice: % of discharges with HomePractice follow-up visit within 7 days | Process | Claims, tool | 158 | | • | | | | ☑ | | | 50 |
| TOTAL Measures | | | - | 4 | 5 | 2 | | 5 | 2 | 4 | | 11 |
| TOTAL Points | | | - | 400 | 375 | 225 | | 650 | 250 | 100 | | 1,000 |
| % | | | - | 40 | 38 | 22 | | 65 | 25 | 10 | | 100% |

FIG. 24

| Structure | | | | | |
|---|---|---|---|---|---|
| | | Program<br>i.e. an<br>"Accountability" | Program Fees ($ pmpm)<br>MD / CH / TP<br>Doctor / CareHub / Training | | Shared<br>Savings |
| Base<br>Program <u>2501</u> | | FCC | $1.00 / $0.50 / $0.20 | | ER<br>Admissions |
| Additional<br>Programs <u>2502</u> | | Asthma | Additional Fees (proforma)<br>n/a / n/a / n/a | | ER |
| | | Ambulance | $0.05 / n/a / $0.02 | | Ambulance |
| | | Imaging | $0.20 / $0.10 / $0.05 | | Imaging |

2503 points to Program Fees

FIG. 25

SYSTEM AND METHOD TO MEASURE AND MANAGE URGENT CARE REQUESTS

CROSS-REFERENCE TO RELATED APPLICATIONS

This application claims the benefit of U.S. Provisional Application No. 61/352,439, filed Jun. 8, 2010, the entire disclosure of which is incorporated by reference herein.

FIELD OF THE DISCLOSURE

This disclosure relates to software for tracking, assessing and managing requests for medical services and delivery of those services. More particularly, the disclosure relates to software for use by primary care physicians (PCPs) and their staff to measure and manage urgent care requests and access to care (i.e. fulfillment of care requests) and care coordination, and thus improve the quality and efficiency of care delivery while reducing avoidable emergency room (ER) visits and avoidable hospital admissions. This software may also be used by healthcare payers and purchasers for the configuration, operation, monitoring and analysis of quality and efficiency improvement programs.

BACKGROUND OF THE DISCLOSURE

Studies have shown that approximately 40% of ER visits are avoidable. From 1996 through 2006, the annual number of ER visits increased 32% and the average wait time increased to 56 minutes. In the year 2000 there were nearly 5 million potentially preventable admissions to US hospitals, resulting in $26.5 billion of excess costs. It is estimated that a modest 5% decrease in hospitalizations for ambulatory care sensitive conditions would save more than $1.3 billion.

Most ER visitors do have medical insurance and thus a regular place for primary care. Despite this, many patients do not use their primary care physician (PCP) for urgent care (that is, care that is needed within 48 hours). PCPs are often not available for urgent care because they fill their day with pre-planned visits in order to maximize revenue. Lack of primary care for urgent needs causes over-utilization and over-crowding of the ER. Over-crowding in the ER causes decreased clinical quality. PCPs lack the tools and incentives to improve this situation. Meanwhile, health insurers have been reluctant to provide financial incentives to physicians to improve performance without independent proof of physician performance.

Over-utilization of the ER is largely the result of poor access to care for urgent care needs (care that is needed within 48 hours). Problems with health-system barriers to care (that is, restrictions on access to care) increased approximately 9% between 2003 and 2007. In particular, many Medicaid patients are unable or unwilling to use their local Federally qualified health center (FQHC) for urgent care due to access problems. These problems generally fall into these categories:

(1) Structural issues at FQHCs: limited office hours; insufficient PCP capacity resulting in long wait times and lead times; inefficient scheduling practices; inefficient workflow within FQHCs.

(2) Patient-Provider Interactions: communication problems due to literacy and foreign languages; limited patient understanding as to the appropriate use of ERs and FQHCs for urgent care.

(3) Financial Issues: lack of financial incentives for either the FQHCs/PCPs or patients to change behavior.

(4) Externalities: factors outside the scope of delivery of medical care, such as the lack of convenient local transportation.

Many avoidable hospital admissions are re-admissions which result from poor discharge coordination between the hospital and the PCP; the lack of timely follow-up by PCPs; poor communications between the hospital and the patient; and lack of understanding by the patient. Studies in the state of Connecticut show that readmissions within 30 days of a prior hospitalization increased from approximately 10% of total discharges in FY 2004 to over 13% in FY 2009. Twelve percent of Medicaid discharges were readmitted within 30 days of discharge. The leading causes of preventable hospitalizations typically are: congestive heart failure; bacterial pneumonia; diabetes; urinary tract infections; chronic obstructive pulmonary disease; and asthma.

Previous attempts to address the problem of over-use of ERs have had limited success. Insurance companies have asked patients to bear a significantly greater portion of the cost through higher co-pays or deductibles. This has not been an effective deterrent because there are few alternatives for urgent care. Likewise, attempts to address the issue from the physician side have been hampered by the perverse incentives of the fee-for-service payment system and by the inability to measure what, if anything, physicians are doing about improving "access" (other than through the use of annual questionnaires of questionable reliability).

Having a regular place for primary care (a "Medical Home") has been shown to increase quality and reduce avoidable ER and admissions and is the core concept of the Patient-Centered Medical Home model (PCMH), which is an important component of healthcare reform efforts nationwide. The PCMH model has shown promise for solving the problems of urgent access, avoidable ER visits and avoidable hospital admissions. However, it has proven difficult and expensive to implement for both PCPs and managed care organizations (MCOs), due to the comprehensiveness of the required capabilities, the cost of developing and providing those capabilities, and the many years required to generate a return on investment. These issues are significant barriers to adoption of the PCMH model by PCPs and financial support for the PCMH by MCOs.

More generally, in the current U.S. healthcare system there is little accountability for outcomes. This has in turn inhibited efforts to reform the payment system. Competition in the U.S. healthcare system is based largely on size and market power, rather than quality or value (defined as outcome divided by cost). Measurement of the quality of health care delivery, and rewards for those who deliver high-quality care, depends on accurate information. The fragmented nature of the health care delivery system in the U.S. makes accurate measurement of a provider's performance very difficult. This is apparent from several points of view: patients, providers, and payers. FIG. 1A illustrates a typical situation where patient 100 seeks care from two different PCPs 101, 102, and also seeks care at an ER 103. Claims from all three providers are submitted to payer 110. Each provider has only a limited view of the patient's overall condition, or the reason for each particular visit. The payer sees an aggregate of the providers' claims, but generally does not have any view of the relationship between those claims, or what initiated a given visit. In caring for a panel of multiple patients 201 (FIG. 1B), a provider 200 must present claims to a plurality of payers 210, 220, 230. The payers typically have different procedures and workflows (schematically illustrated at 211, 221, 231). None of the payers has an accurate view of the relationship between the claims, or of the patient's overall condition. This prevents determining the outcome and quality of care from claim information. An individual payer 300 (FIG. 1C) typically interacts with multiple care providers 310, 320, 330, but has a view of only a fraction of each provider's business (schematically illustrated at 311, 321, 331). This situation makes statistically valid measurement of provider performance difficult or impossible. In addition, improvements in the payer's workflow will have only a limited impact on the delivery of a given provider's care.

In order to measure the quality of care a certain provider delivers to a patient or group of patients, a current and accurate roster of the provider's patients must be constructed, thereby documenting the patient-to-physician (P2P) relationship; this is referred to herein as P2P attribution. Inaccurate P2P attribution by health plans for the purpose of determining and then tiering physicians based on clinical quality and efficiency—and subsequent public assertions of superior (or inferior) quality and the payment (or withholding) of financial incentives—is a major problem and the cause for numerous lawsuits by medical societies and state governments against health plans.

Most P2P attribution methodologies use historical claims data to assign P2P attribution based on: (a) the most recent patient visit; (b) preponderance of visits in a given period; or (c) preponderance of costs. All of these methodologies have been shown to have significant shortcomings. In addition to the particular problems with each methodology, all of these are retrospective; that is, they try to establish who will be responsible for care based on who theoretically was responsible for care—an often inaccurate assumption.

A claims-based P2P attribution methodology is unsatisfactory because the claims system was not designed to capture P2P information, is incapable of providing timely feedback to physicians, and is ignorant of both the physician's perspective on P2P attribution, and ignorant of the patient's wishes. Furthermore, as P2P relationships are dynamic, P2P attribution methodologies must also be dynamic and able to adjust in real-time—something the claims system cannot accommodate due to the typical 30- to 90-day processing delay.

Physicians in small and fragmented (i.e. un-affiliated) practices make up the majority of the healthcare delivery system, but have lower quality scores and participate less frequently in quality improvement initiatives than do physicians in large integrated practices; this results in quality, safety, and cost problems relating to health care delivery by those small practices.

Previous attempts to engage small physician practices in continuous quality improvement—such as those by the Institute of Healthcare Improvement (IHI) or federally-sponsored Quality Improvement Organizations (QIOs)—have not succeeded to the degree the U.S. healthcare system needs because participation has been too onerous for small practices for a variety of reasons, including: data collection problems; the costs of providing or attending traditional programs; lack of statistically valid data/analysis and feedback; lack of integration into workflow; and the lack of financial incentives from health insurers. In other words, small physician practices typically lack the means, motive, and opportunity to engage in continuous quality improvement. There have been uncoordinated efforts to address these shortcomings. For example, pay-for-performance (P4P) initiatives may offer financial incentives, but not the tools needed to improve performance. Learning collaboratives offer good advice on process improvement, but rarely offer financial incentives or sustainable data collection processes.

Moreover, the absence of reliable measurements of healthcare quality is having a negative effect on the supply of new PCPs and PCP incomes. While the growing and aging U.S. population requires more PCPs, a shortage of PCPs is developing—an undesirable inverse relationship of supply and demand. An important reason for this is that the present fee-for-service payment system has negatively affected primary care, because PCPs have not been able to effectively prove the clinical and financial value of good primary care.

There is a need to provide PCPs with tools and financial incentives to better manage urgent care requests and thereby provide better service while reducing avoidable hospital utilization (ER and re-admissions) and costs. In particular, there is a need for an improved system, consistent with the PCMH model, for measuring the performance and value of services actually delivered to patients, thereby providing independent proof of PCP efforts to improve urgent access and coordination, and thus enabling the payment of financial incentives to PCPs.

SUMMARY OF THE DISCLOSURE

The present disclosure addresses the above-described need by providing an innovative tracking software system, referred to herein as CareHub™ which provides independent proof of PCP efforts to improve urgent access and coordination. In accordance with the disclosure, PCPs are provided with tools and financial incentives to better manage urgent care requests and thereby provide better service while reducing avoidable hospital utilization (ER and re-admissions) and costs. Measurements of provider performance may be used by payers and purchasers. In particular, independent and accurate measurements of provider performance enable the payment of financial incentives to PCPs.

According to one aspect of the disclosure, CareHub is web-based software delivered to users via the internet; accordingly, no software is installed or downloaded onto the user's computers. CareHub is advantageously built in a modular fashion to enable the use of industry standard components from a wide selection of component vendors, includes all appropriate privacy and security protections, and is HIPAA-compliant.

A method in accordance with the disclosure, executed on a computing device, includes accessing clinical data and medical claims data relating to care for a group of patients. Relationships are established between patients and providers, where the patients are on a list of eligible patients and the providers are in a directory of providers. This is done by attributing a patient to a provider in accordance with the medical claims data and/or a predetermined rule; and requesting confirmation from the provider regarding a patient-provider relationship with the patient. Clinical events related to an urgent care request are recorded; these events include an initial communication requesting care, and fulfillment of the request. Performance of the provider of the care is measured with respect to at least one predetermined criterion.

In accordance with particular embodiments of the disclosure, CareHub™ is a software platform with extension modules; these are used by PCPs and their staff to measure and manage urgent care requests and fulfillment ("access to care") and care coordination, and thus improve the quality and efficiency of care delivery while reducing avoidable Emergency Room (ER) visits and avoidable hospital admissions.

In an embodiment, the software includes the CareHub platform, a Physician Attribution Information and Reconciliation™ (PAIR™) module, a Tracking module, an Analysis and Rewards module, a Data-Driven Interactive Learning Environment™ (DD-ILE) module, a Registry module, and a Patient Portal/Public Reporting module. Each module can be a stand-alone product, or combined with other modules and the platform for a complete solution. The software advantageously also includes CareHub-MobileAccess™ (CH-MA) software enabling mobile-phone-based use of the system.

The foregoing has outlined, rather broadly, the preferred features of the present disclosure so that those skilled in the art may better understand the detailed description of the disclosure that follows. Additional features of the disclosure will be described hereinafter that form the subject of the claims of the disclosure. Those skilled in the art should appreciate that they can readily use the disclosed conception and specific embodiment as a basis for designing or modifying other structures for carrying out the same purposes of the present disclosure and that such other structures do not depart from the spirit and scope of the disclosure in its broadest form.

BRIEF DESCRIPTION OF THE DRAWINGS

FIGS. 15A and 15B are screenshots illustrating an implementation of a procedure for assessing an urgent care request in the process of FIG. 11.

FIG. 16 is a screenshot illustrating an implementation of a procedure for assigning the urgent care request to a provider in the process of FIG. 11.

FIG. 17 is a screenshot illustrating an implementation of a procedure for follow-up after the urgent care request in the process of FIG. 11.

FIGS. 18A-18C are screenshots illustrating implementation of care access management in accordance with an embodiment of the disclosure.

FIGS. 23A-23E are screenshots illustrating an implementation of reporting provider performance in responding to urgent care requests, according to an embodiment of the disclosure.

FIG. 24 is a matrix of processes and outcomes which may be measured using a system embodying the disclosure.

FIG. 25 shows additional programs (accountabilities) in which provider performance may be measured using a system embodying the disclosure.

DETAILED DESCRIPTION

Introduction

The CareHub system and method, embodiments of which are described below, permits measurement and payment for healthcare outcomes. The CareHub system and method measures service management (e.g. access to provider(s) of care and coordination of care) across healthcare entities; these measurements are enabled despite the fragmentation of healthcare delivery.

Figure 1A:
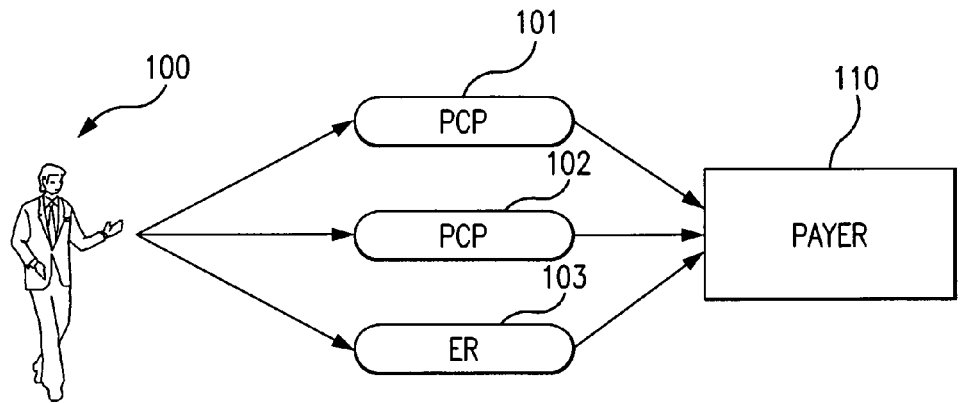
FIGS. 1A-1C schematically illustrate typical situations where information regarding quality of healthcare is fragmented, from the point of view of a patient, provider and payer.
Figure 1B:
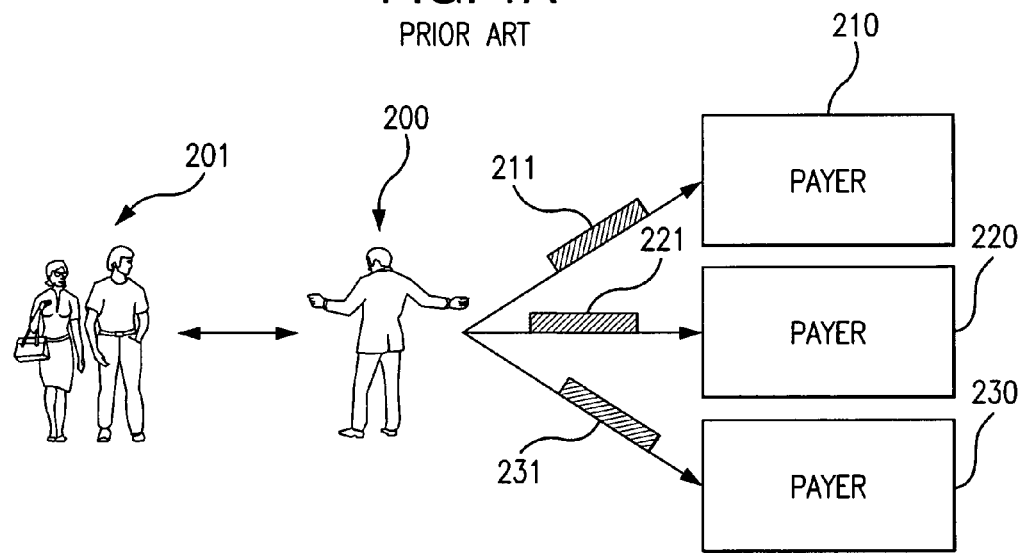
Figure 1C:
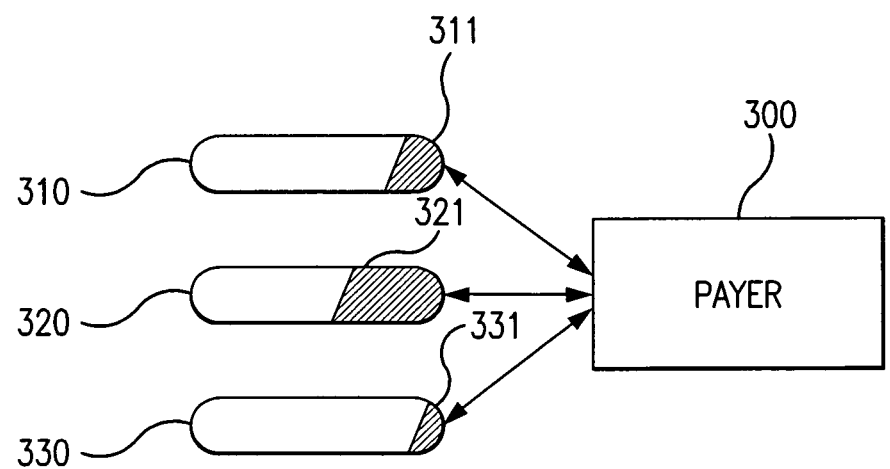
Figure 2:
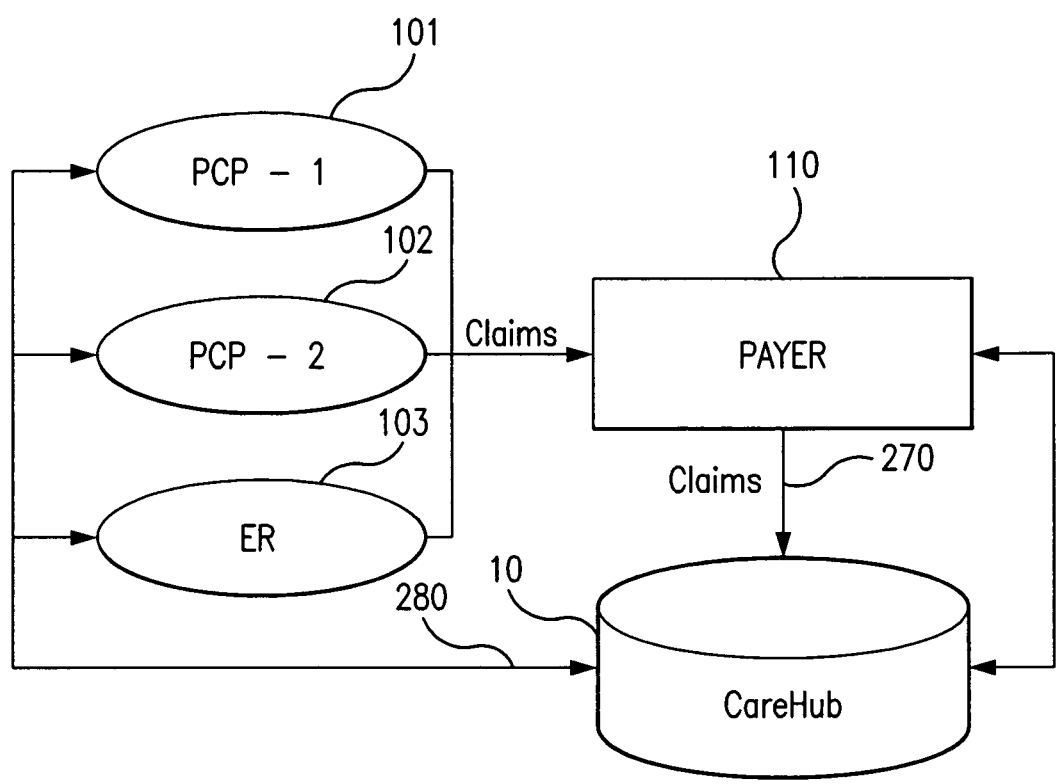
FIG. 2 schematically illustrates an embodiment of the disclosure in which the CareHub system exchanges information to payers and providers.

As shown schematically in FIG. 2, the CareHub system 10 interfaces with the care providers 101, 102, 103 and payer 110. The system 10 imports claims data 270 from payer 110 and service management data (including clinical data) 280 from the providers. Using a combination of data permits accurate assessments of various aspects of the providers' performance. Information and analysis is fed back to the providers and the payer to improve performance, and for calculation and payment of rewards for high-quality performance.

Figure 3:
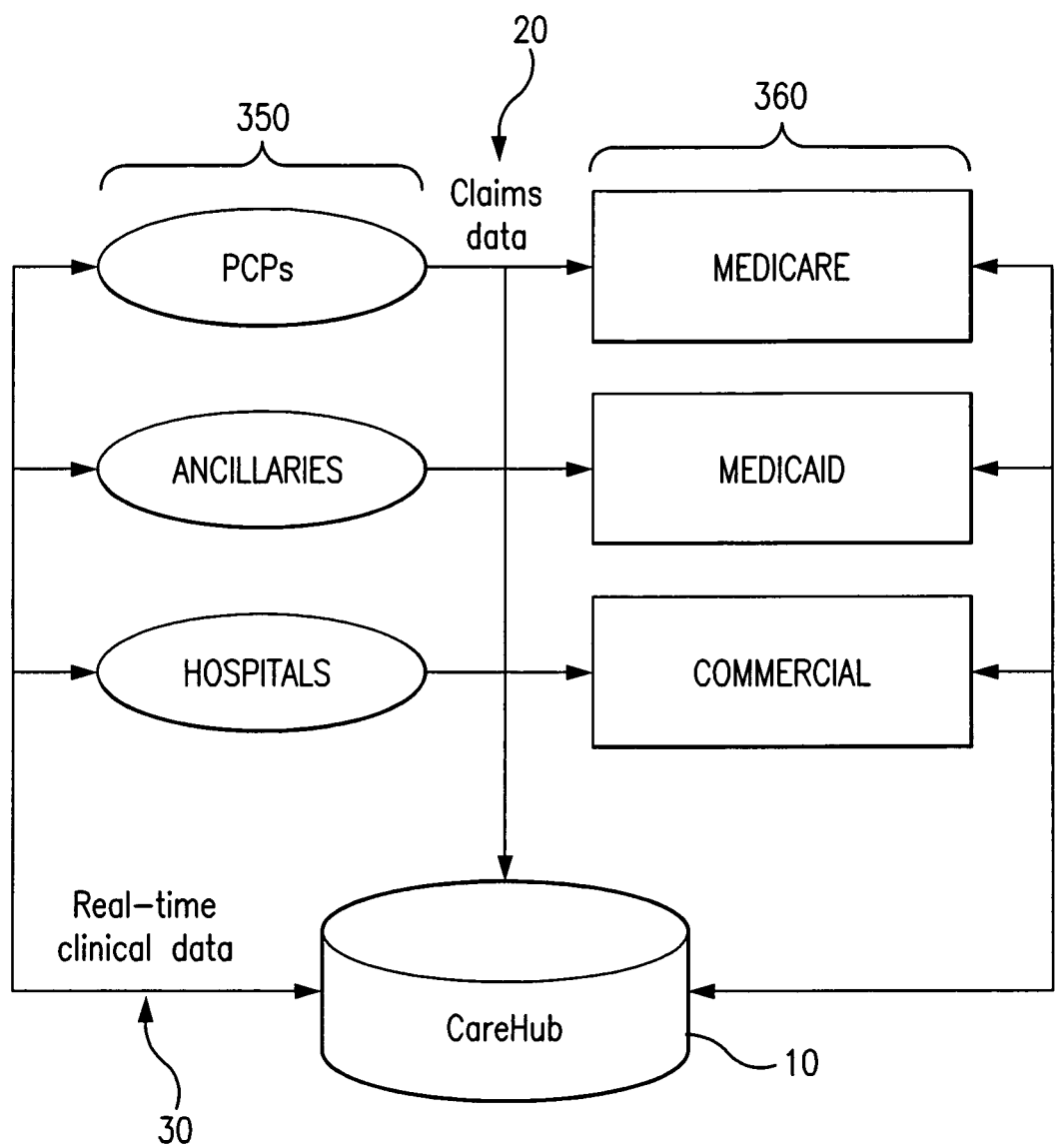
FIG. 3 schematically illustrates an embodiment of the disclosure in which the CareHub system imports claims data and real-time clinical data.

More generally, as shown in FIG. 3, data from several providers representing different systems of care 350 and from several payers representing different payment systems 360 are gathered by the CareHub system 10. The data includes claims data 20 and real-time clinical data 30.

Figure 4:
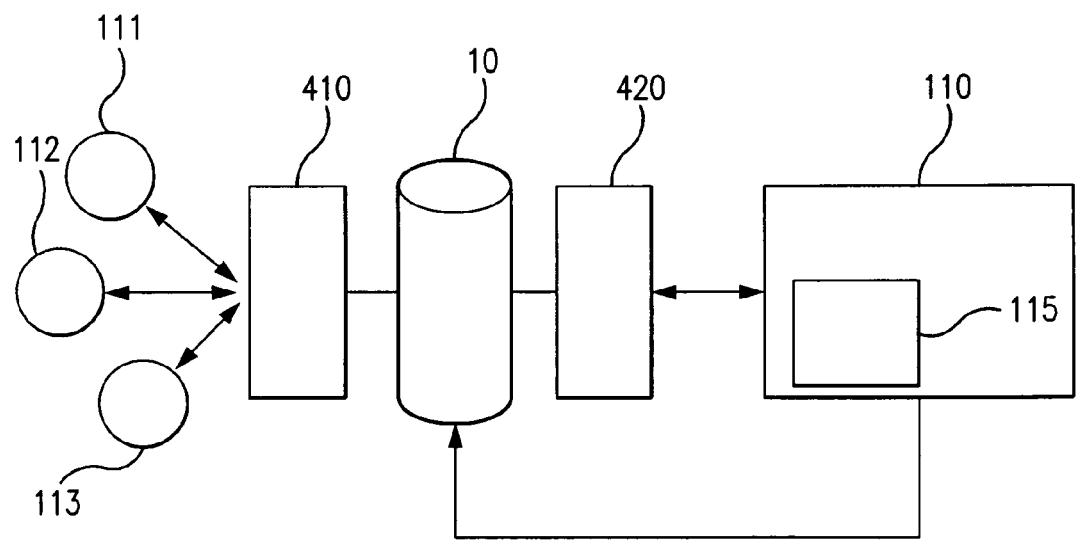
FIG. 4 schematically illustrates user interfaces for the CareHub system, in accordance with the disclosure.

In an embodiment, system 10 has two user interfaces 410 and 420 for communicating with providers and payers respectively (see FIG. 4). Providers (for example, PCPs 111, 112, 113) access the user interface 410 and transmit service management data to system 10. A payer 110 typically has its own database 115 for managing and storing claims data. Claims data may be directly imported by system 10 from payer 110.

Figure 5:
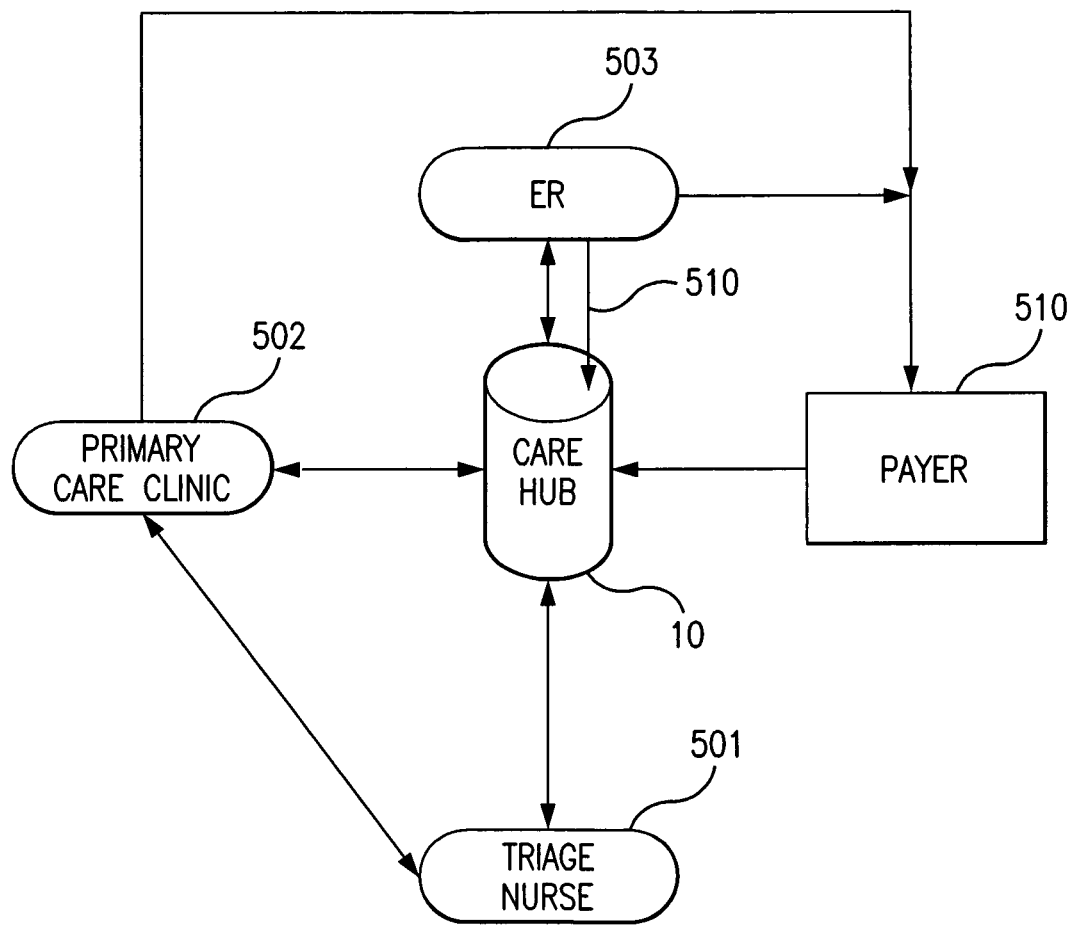
FIG. 5 schematically illustrates an implementation of the CareHub system in accordance with an embodiment of the disclosure.

An embodiment of the disclosure implemented in a hospital is schematically illustrated in FIG. 5. CareHub system 10 exchanges data via user interfaces with triage nurse 501, primary care clinic 502, ER 503 and payer 510. Triage nurse 501 submits patient data and may view triage reports; CHC 502 submits patient data and receives performance reports; ER 503 submits patient data and receives ER utilization and triage reports. The CHC and ER both provide claims data to payer 510, which is imported by CareHub system 10.

Overview of System and Method

Figure 6:
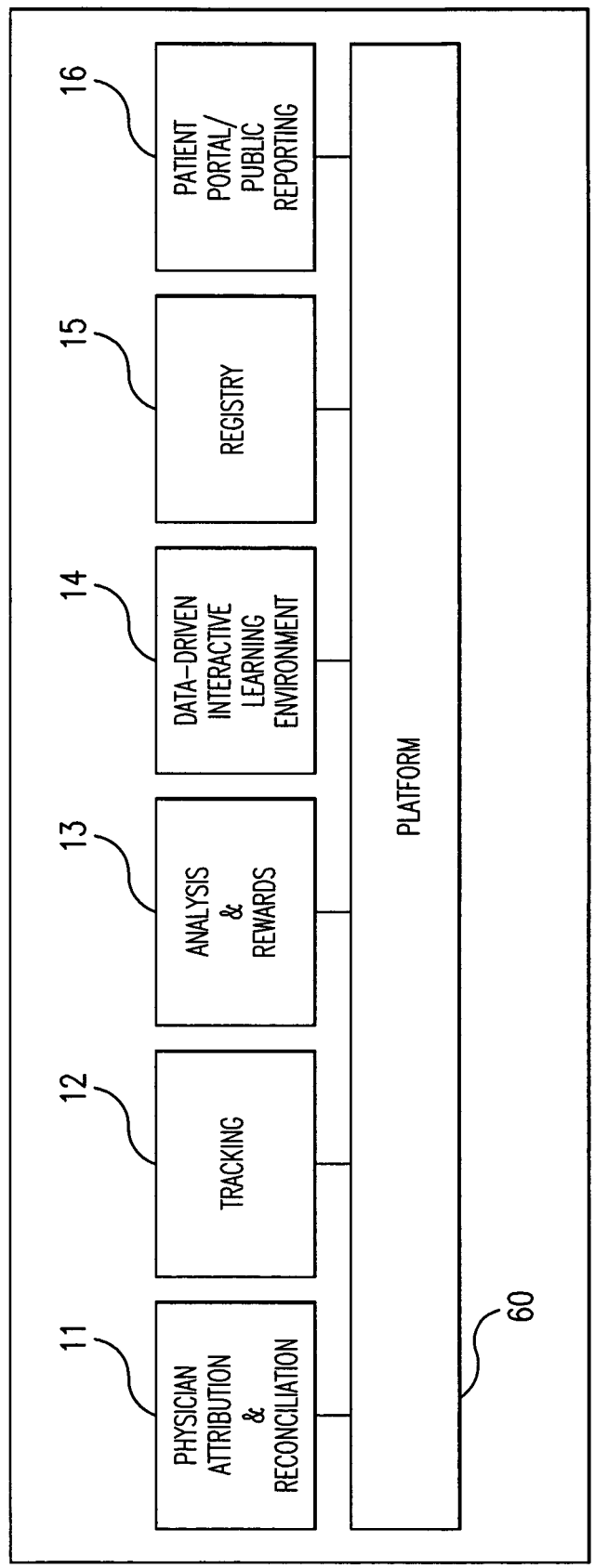
FIG. 6 is a block diagram of the architecture of a CareHub system embodying the disclosure.

In the embodiments described herein, the CareHub system 10 includes a platform 60 linked to several modules, as shown schematically in FIG. 6. The CareHub platform is typically implemented as a web-based system, to which PCPs may connect via their desktop computers. The modules include the Physician Attribution Information and Reconciliation™ (PAIR™) module 11, the Tracking module 12, the Analysis and Rewards module 13, the Data-Driven Interactive Learning Environment™ (DD-ILE) module 14, the Registry module 15, and the Patient Portal/Public Reporting module 16. Each module can be a stand-alone product, or be combined with other modules and the platform.

Figure 7:
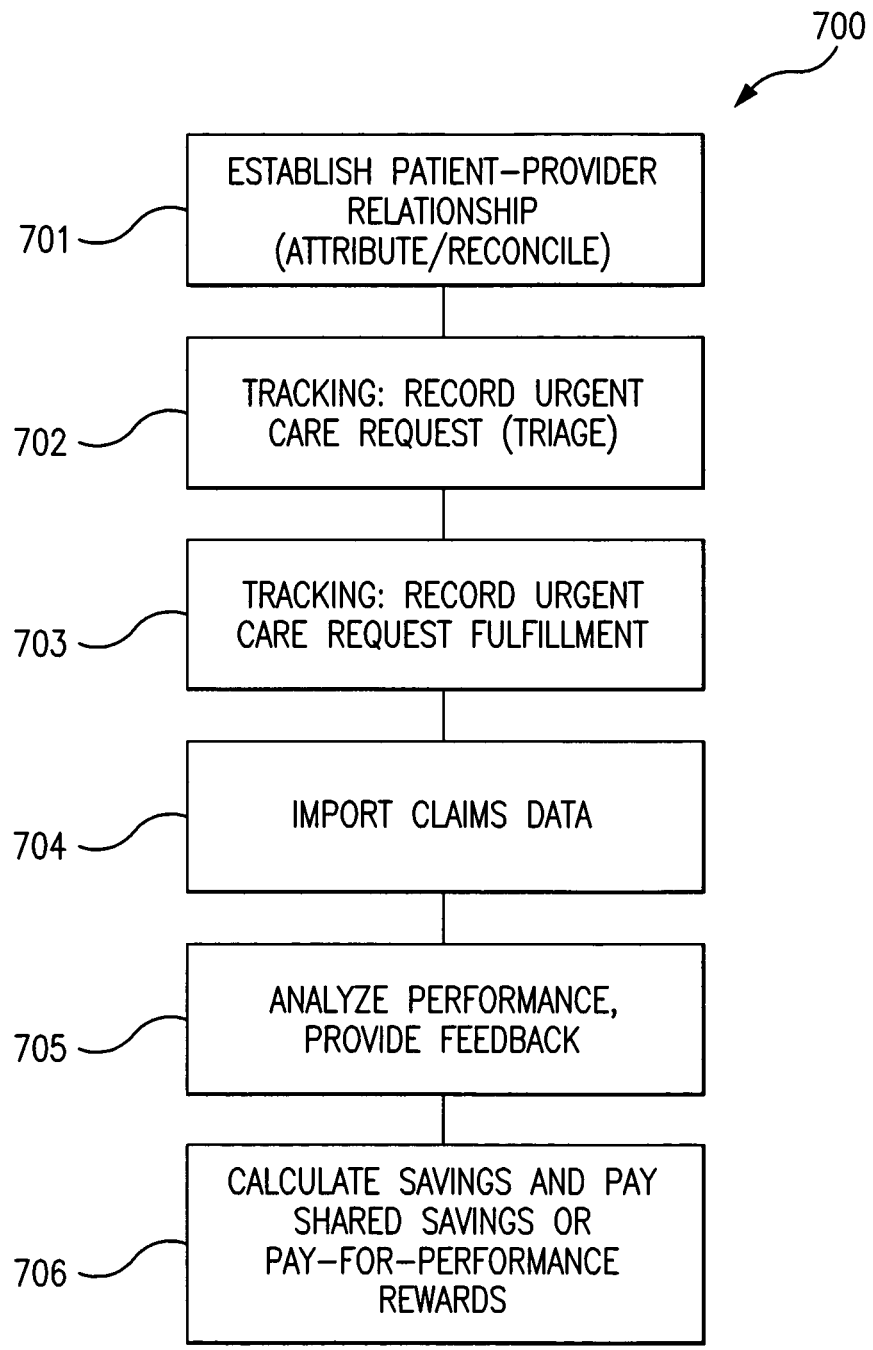
FIG. 7 is a flowchart showing a process for P2P attribution, tracking and management of urgent care requests, analysis of providers' performance, and calculation of rewards for performance, in accordance with the disclosure.

Management and tracking of urgent care requests is performed using a procedure 700 as shown in the flowchart of FIG. 7. In step 701, the relationship between a given patient and a provider (the Medical Home PCP or some other provider) is established by a patient attribution and reconciliation process. Conflicts across providers regarding which provider a patient belongs to (patient attribution) are resolved using a reconciliation process, details of which are discussed below. In step 702, an urgent care request is recorded and tracked, and triage information is gathered and entered (for example, a working diagnosis, assignment to an individual provider, proposed treatment, etc.). After the care is provided, fulfillment of the urgent care request is recorded (step 703) along with data related to the care (for example, a final diagnosis, date and time of treatment, by whom treated, etc.). Claims data is then imported (step 704) and the provider's performance is analyzed using a combination of the claims data and the real-time clinical data (step 705). The system provides feedback to the provider(s) and payer(s) regarding the performance, or improvement in performance. The system then calculates the cost savings resulting from the provider's performance (step 706) and distributes rewards to the participants. The rewards may be shares of the net savings, or pay-for-performance (P4P) rewards.

Physician Attribution and Reconciliation

The Physician Attribution Information and Reconciliation module 11 generates a P2P attribution record for each provider, thereby documenting the patient-to-physician relationships. This module also facilitates reconciliation of gaps and overlaps in P2P relationships (situations where no providers or multiple providers, respectively, have a P2P relationship with a patient). The module generates an accurate and continuously-updated P2P attribution record, thus promoting fairness in making quality and efficiency calculations regarding delivery of care.

Figure 8A:
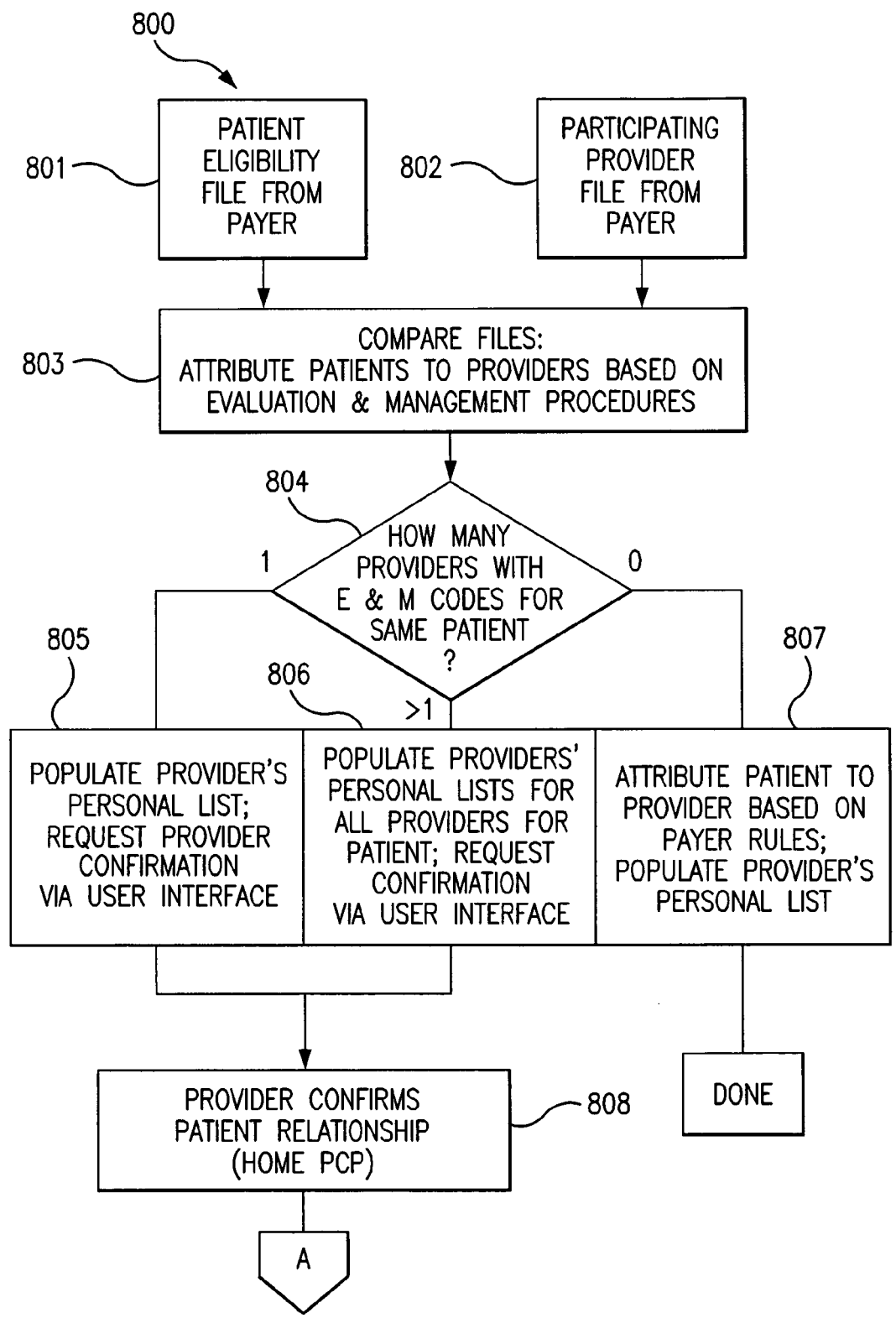
FIGS. 8A and 8B are connected flowcharts showing further details of a P2P attribution and reconciliation procedure according to an embodiment of the disclosure.
Figure 8B:
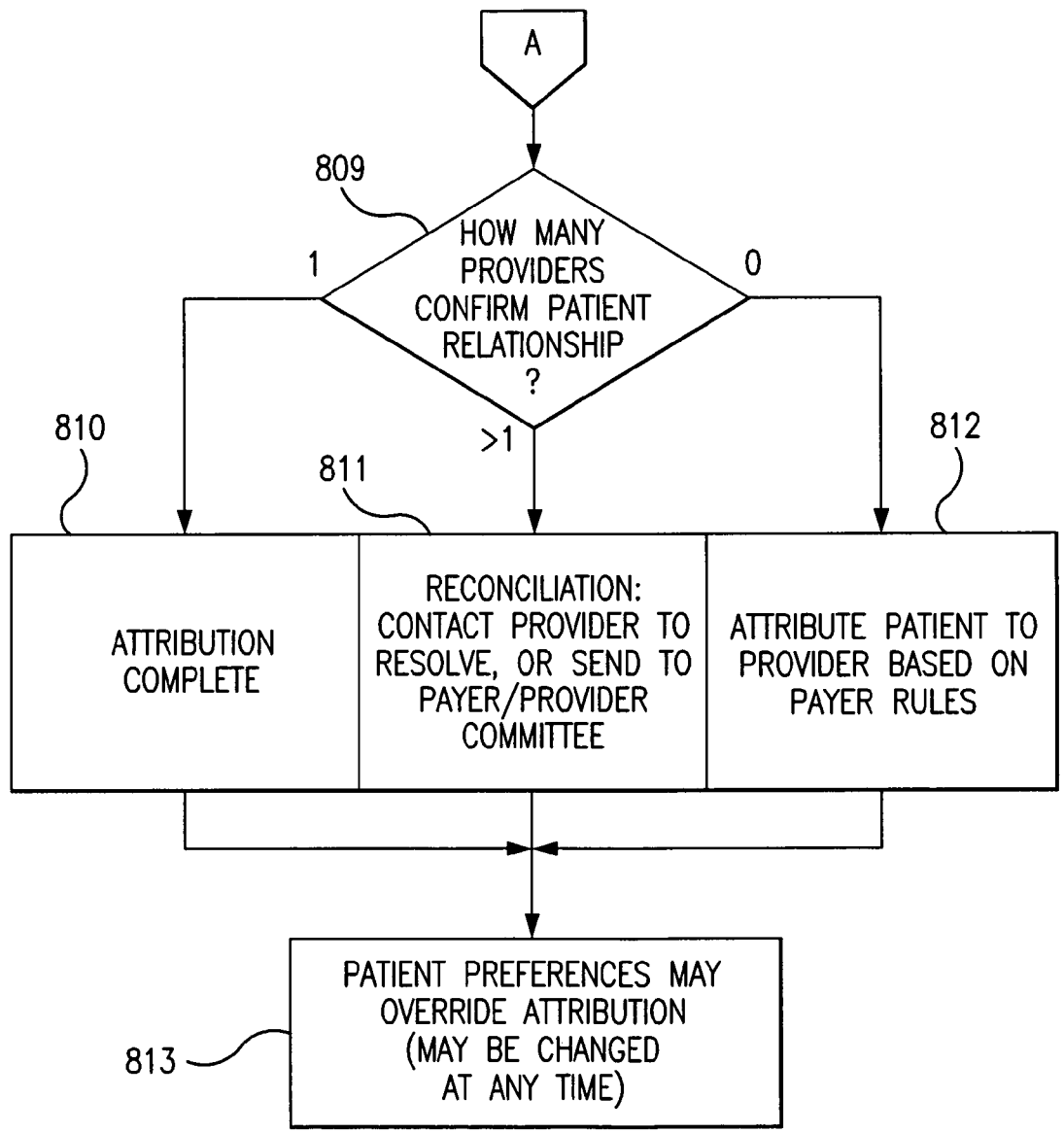

A process 800 for physician attribution and reconciliation, according to an embodiment of the disclosure, is shown in FIGS. 8A and 8B. The module obtains the patient eligibility file and the participating provider directory file from a payer (steps 801-802). The patient eligibility file is typically updated monthly and includes a list of patients who could be enrolled in a medical care program; the participating provider directory file is updated periodically and includes a list of providers (primary care physicians or otherwise) to whom patients may be attributed.

Patients are initially attributed to a given provider based on claims information from the payer (step 803). An insurance claim during a selected past time period (e.g. three years in the case of Anthem, one year in the case of Medicaid) establishes a potential P2P relationship. Claims data from the payer over the selected period is analyzed for codes, typically Common Procedural Terminology (CPT-2) codes, associating a patient with a particular provider (PCP, hospital, nursing home, specialist, etc.). For primary care providers, the claims data typically include Evaluation and Management (E&M) codes. This analysis determines which patients were treated by, and thus could be attributed to, a particular provider.

To attribute a patient to a primary care provider, the module determines (step 804) how many providers have E&M codes for the same patient. If one and only one provider has E&M codes for a patient (indicating that during the selected period, claims relating to the patient arose out of that P2P relationship), the patient is attributed to that provider and the patient is added to a list of patients associated with that provider (step 805). The provider is requested to confirm this attribution via the user interface 410.

If more than one provider has E&M codes for a patient, the patient is added to all of the lists associated with the respective providers (step 806). Each provider is requested to confirm whether the patient should appear on the list for that provider; a provider confirming attribution of a patient takes responsibility for the patient, at least for the specific purposes of the care program. Alternatively, the patient may be attributed to one of the providers using a rule selected by the payer (e.g. provider with the most recent E&M code, provider with greatest number of E&M codes, etc.).

If no provider has E&M codes for a patient (step 807), the patient is attributed to a provider according to rules developed by the payer.

A list of potential patients is presented to each provider who is asked to confirm the P2P relationships (step 808); the provider is asked to "Accept" or "Decline" responsibility for a patient (or for a particular aspect of a patient's care). If one and only one provider accepts responsibility (step 809), then the P2P relationship is established (step 810) (e.g. the provider becomes the patient's Home PCP). If none of the providers accepts responsibility, the patient is attributed to a provider in accordance with the payer's rules (step 812). If more than one of the providers accepts responsibility, then the system moves into the reconciliation process (step 811), in which the patient is attributed to one of those providers. The reconciliation process is conducted according to user-configurable rules. In general, reconciliation is performed by consulting with the provider, a committee of providers and/or payer's representatives, or the patient. The patient's preferences may override an attribution; furthermore, an attribution may be changed at any time (step 813).

Reliance on past claims data for P2P attribution causes the attribution to be retrospective; that is, determining the P2P relationship based on prior events. In an attribution procedure according to the disclosure, the provider confirms the relationship and the patient may override it, so that the P2P relationship is established prospectively. Moreover, the system continuously updates the P2P relationships to reflect changes in the patient eligibility file and the provider directory file and recent consultations or confirmations by providers, committees or patients. It will be appreciated that accuracy in the P2P relationships, thereby indicating a provider's clinical responsibility for a patient, is important in making reliable measurements of a provider's performance.

Figure 9A:
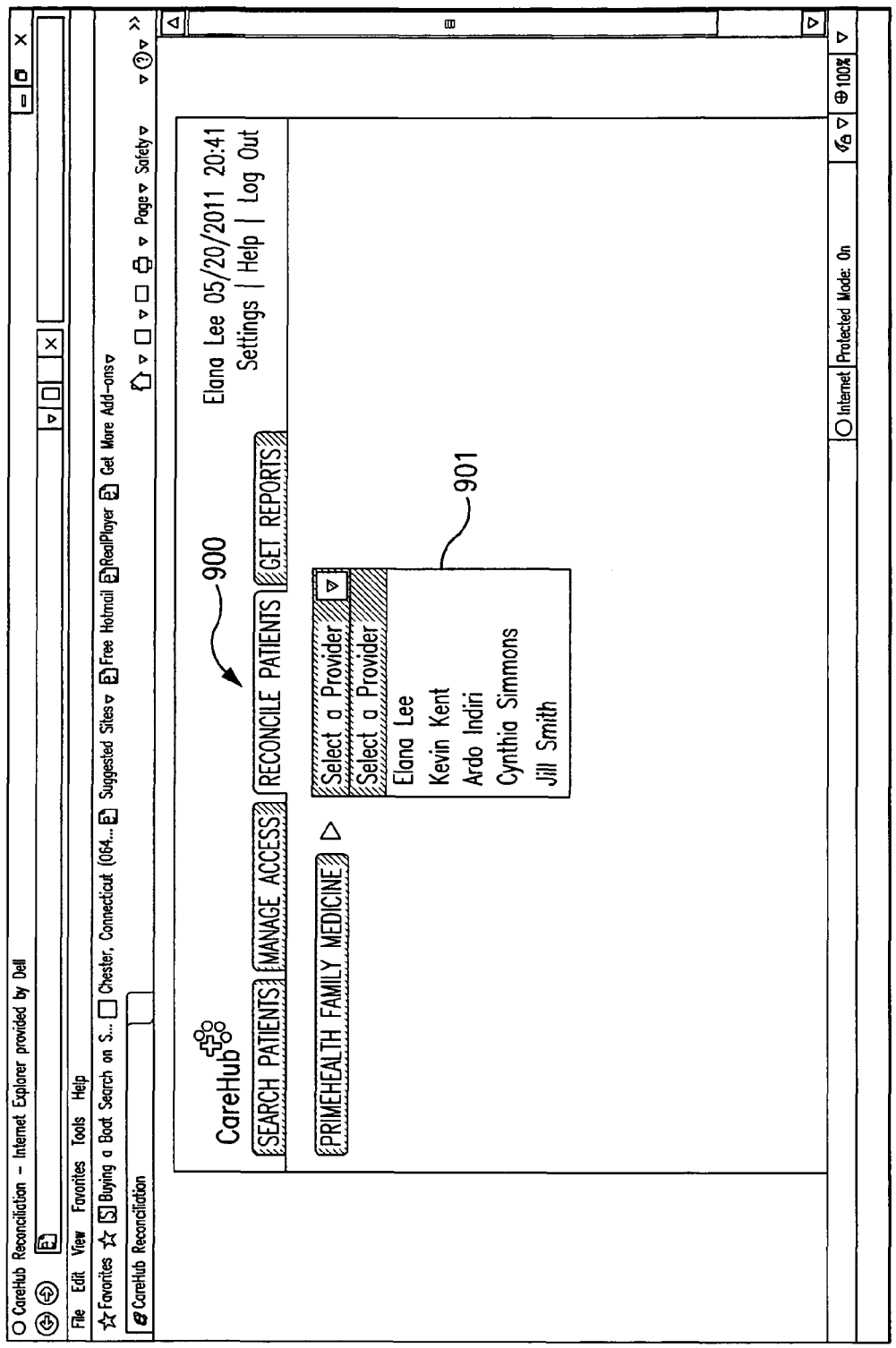
FIGS. 9A-9C are screenshots illustrating an implementation of the P2P attribution procedure of FIGS. 8A and 8B.
Figure 9B:
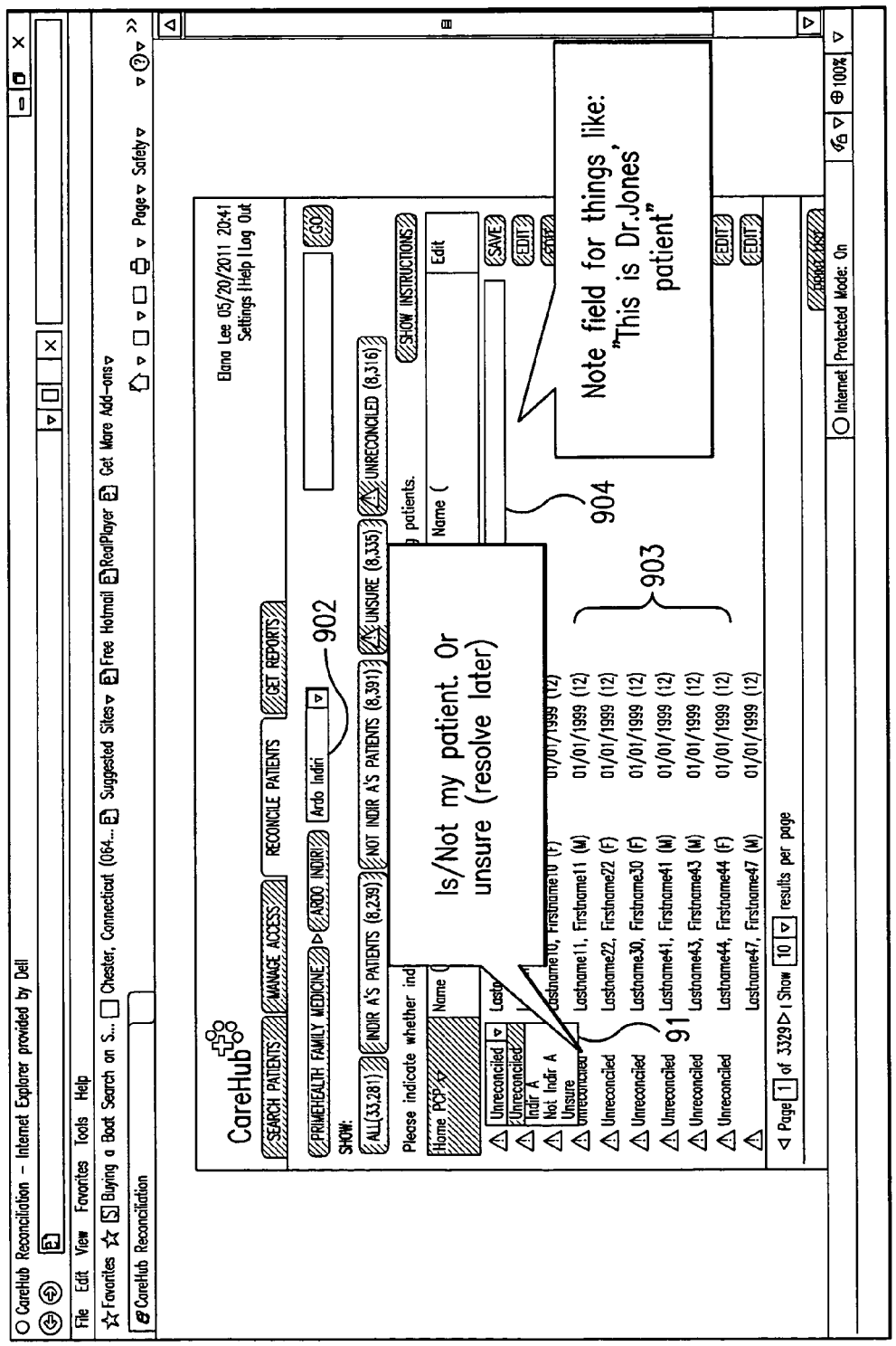
Figure 9C:
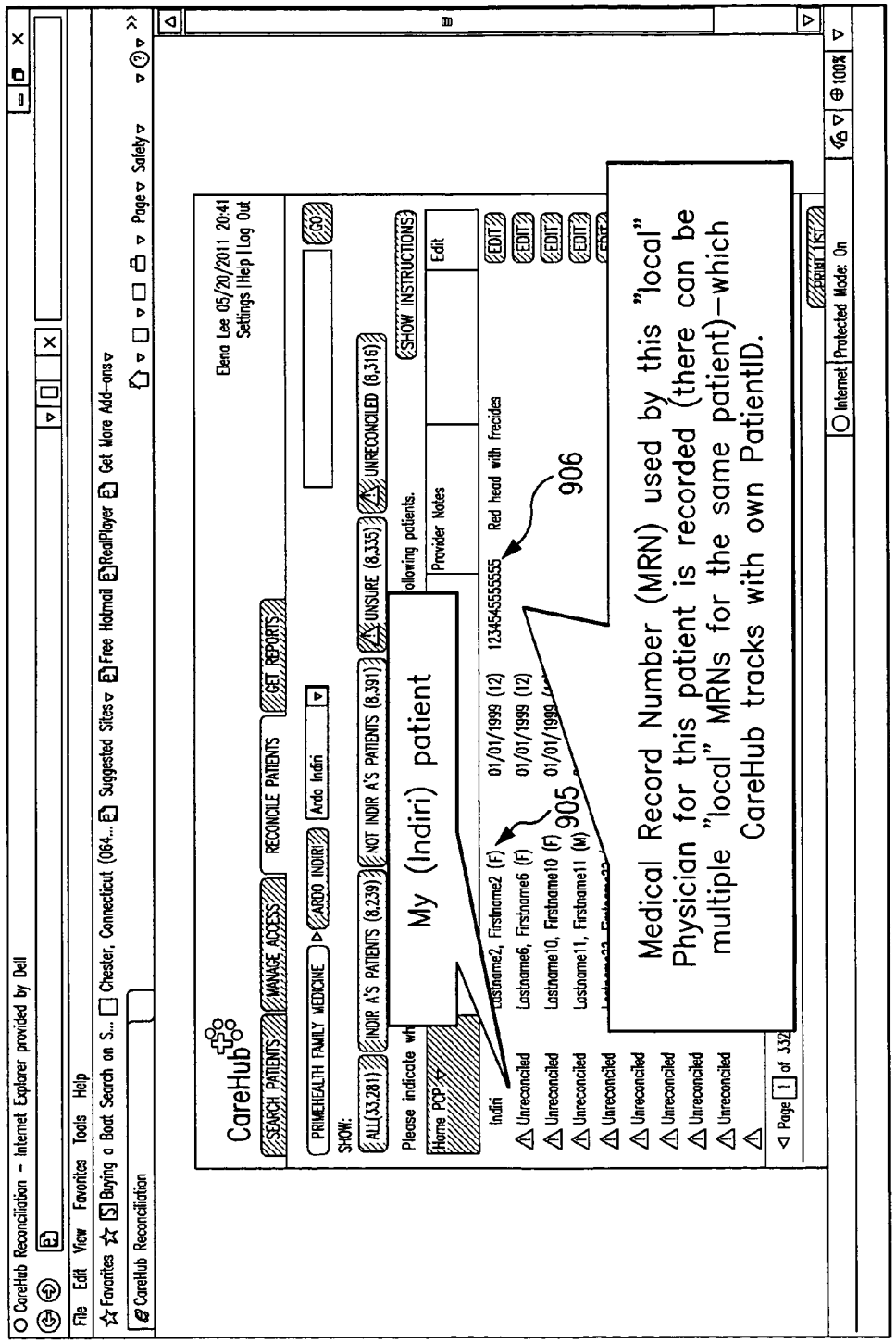

Implementation of an attribution process according to an embodiment of the disclosure is illustrated in FIGS. 9A-9C. As shown in FIG. 9A, the CareHub provider interface 410, at the "Reconcile Patients" screen 900, presents a menu of providers 901 who are users of that CareHub installation. The provider 902 whose name is selected from menu 901 is presented with a list 903 of patients for attribution to that provider (FIG. 9B). For each patient on list 903, the provider uses a menu 91 to indicate whether that patient is or is not his/her patient. A note field 904 permits the provider to make comments, e.g. the name of another provider to whom the patient should be attributed. When a provider accepts a patient 905, the provider's name is listed as "Home PCP" next to the patient's name (see FIG. 9C). The provider may enter a medical record number (MRN) 906. (In this embodiment, there may be multiple MRNs for a given patient, and the system generates an internal ID number for the patient relating the MRNs to each other.)

Figure 10:
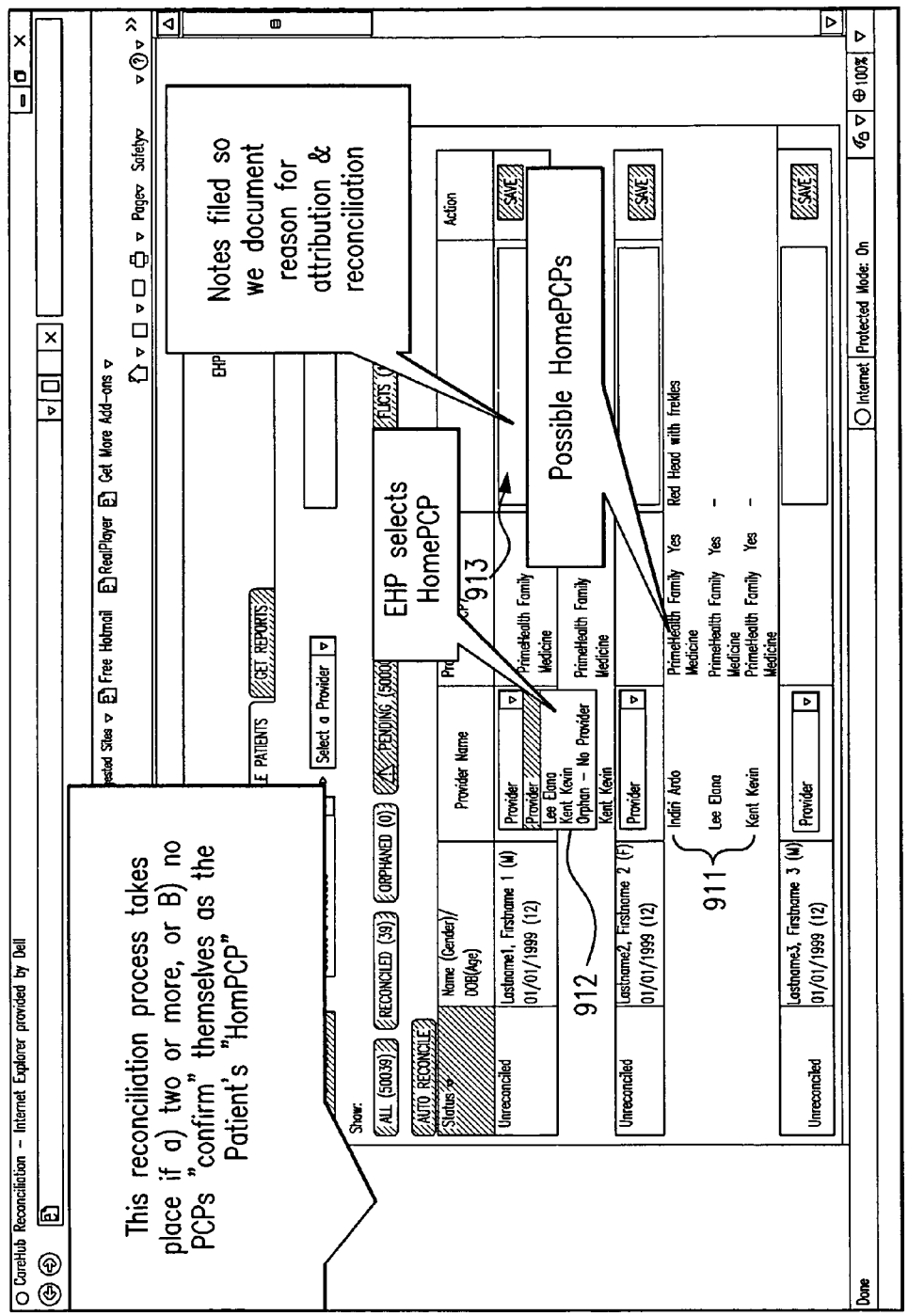
FIG. 10 is a screenshot illustrating an implementation of the reconciliation procedure of FIGS. 8A and 8B.

The reconciliation process resolves overlaps or gaps in the P2P relationships—where either multiple PCPs or no PCPs confirm themselves as the Home PCP for the patient. Implementation of a reconciliation process according to an embodiment of the disclosure is illustrated in FIG. 10. The "Reconcile" screen 910 is presented to an individual authorized to attribute a patient to a particular provider (thereby establishing a P2P relationship). This individual may be a provider, a member of a committee, a CareHub administrator, etc. For each unreconciled patient, a list 911 of possible Home PCPs is displayed, and a Home PCP is selected from menu 912. A notes field 913 permits documentation of the reason for reconciliation of the P2P relationship.

Urgent Care Request Triage and Tracking

The tracking module 12 (FIG. 6) is used to manage and document urgent care requests, and addresses these issues or similar service request and delivery processes:

(1) Which physician/practice received the urgent care request? (Medical HomePCP/Cross-Covering PCP, or other)

(2) When was the Urgent Care Request received? (Office Hours/After Hours)

(3) To whom was care assigned? (Medical HomePCP/Other PCP in same Practice/Cross-Covering PCP or Practice/Walk-In Clinic/Emergency Room/Specialist)

(4) When was the Urgent Care Request fulfilled? (Date that care was provided; Goal: Same day/Next day)

(5) Where was the Urgent Care Request actually fulfilled? (Medical Home PCP/Medical Home Practice/Cross-Covering PCP or Practice/Walk-in Clinic/Emergency Room/Specialist)

(6) When were Hospital Discharges followed-up? (Follow-up date; Goal: within 7 days)

Figure 11:
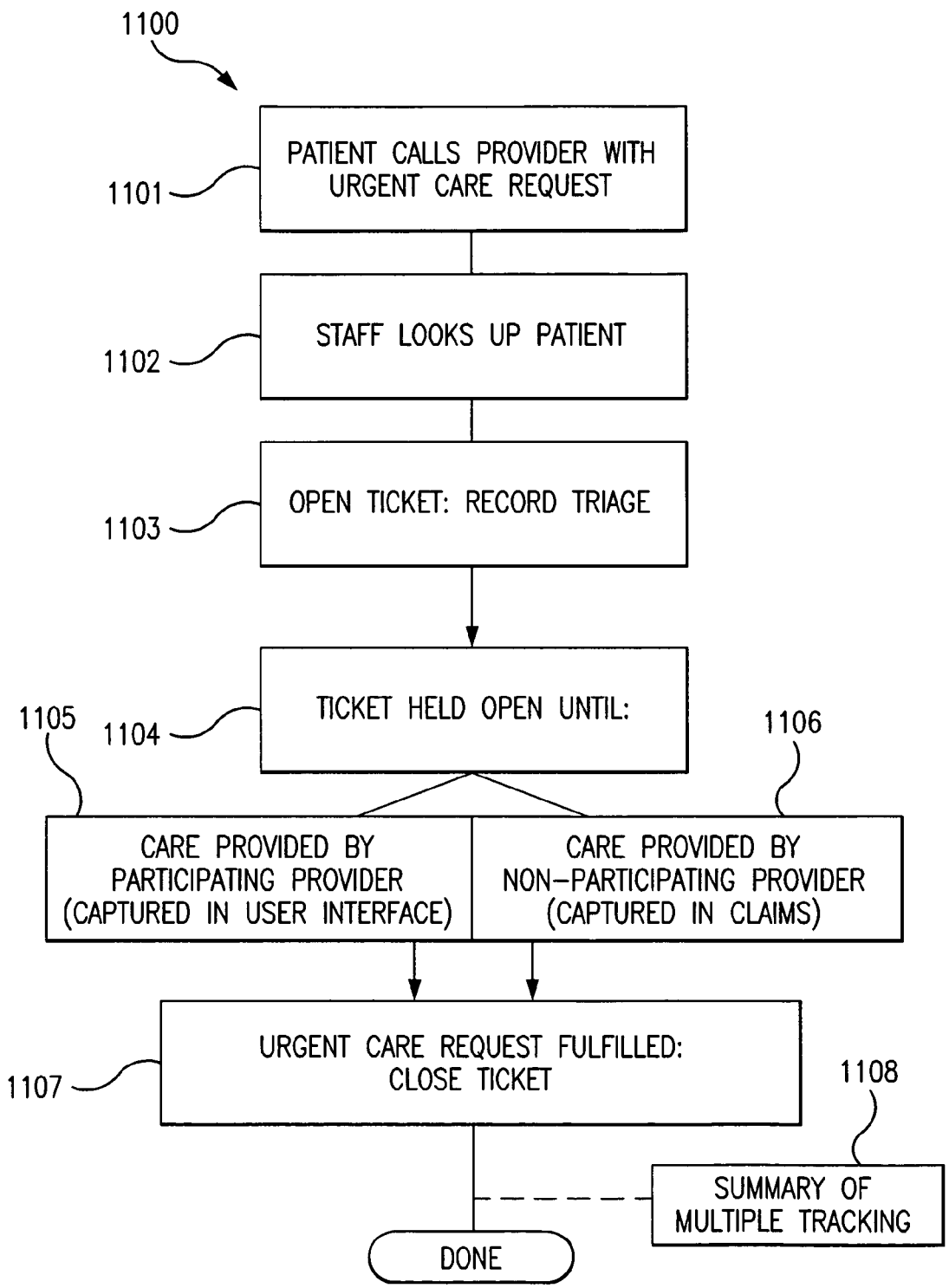
FIG. 11 is a flowchart showing further details of an urgent care request triage and tracking procedure according to an embodiment of the disclosure.

A process 1100 for recording and tracking urgent care requests, according to an embodiment of the disclosure, is shown in FIG. 11. A patient calls a provider (step 1101) to make an urgent care request; the provider's staff looks up the patient in their CareHub records (step 1102). In this example, it is assumed that the patient and the provider have an existing relationship. A record is created for tracking the request and the delivery of care; this is referred to herein as opening a CareHub ticket (step 1103). In this embodiment, the date and time of opening the ticket are captured automatically, and the name of the person initiating the ticket is noted. The provider (in this example, the Home PCP or staff) triages the request, documenting the urgency of the request and a working diagnosis. The request is then assigned to a particular provider for delivery of care.

The ticket is held open (step 1104) until care is provided. If the care is provided by a participating provider (step 1105), that event is documented using the CareHub interface. If the care is instead provided by a non-participating provider (step 1106), information regarding delivery of care is captured from claims data. The ticket is closed (step 1107) when the urgent care request is fulfilled, e.g. care is provided, or is no longer needed. The request is tracked (step 1108) through several stages of completion (assessment, assignment, etc.) and tracking summaries are displayed, as shown for example in FIG. 18B.

Figure 12:
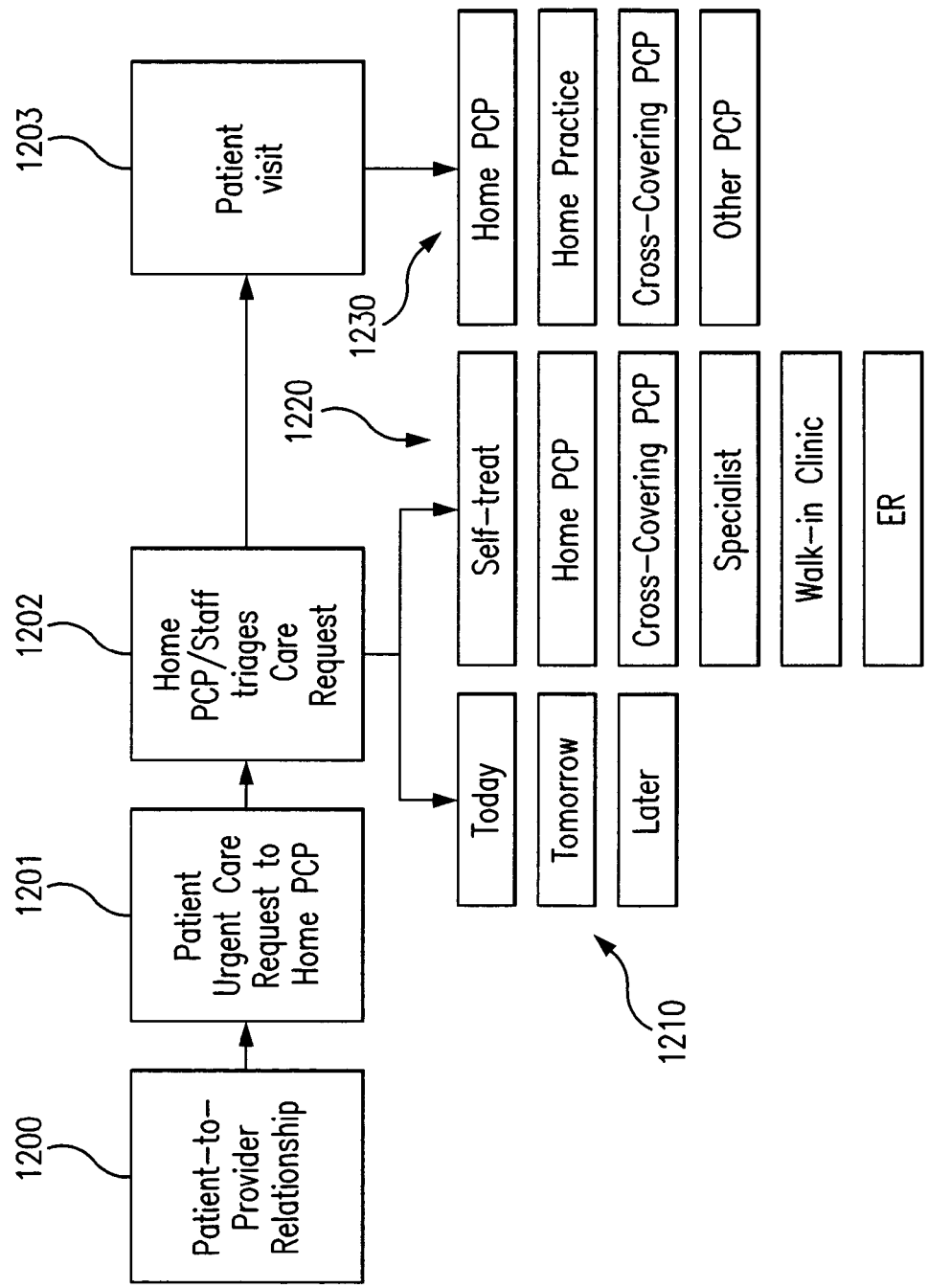
FIG. 12 illustrates a situation where a patient visit is documented only retrospectively in claims data.

Reliance on claims data does not, in general, permit measurement of the response to the urgent care request or of the quality of urgent care. The importance of tracking the request through triage to fulfillment is illustrated in FIG. 12. A patient having an existing relationship 1200 with a Home PCP may make an urgent care request 1201 to that provider, which then triages the care request. However, the patient typically makes a visit 1203 (documented in claims data) to the provider at an indefinite later time (indicated by the arrow from 1202 to 1203). The triaged care request 1202 may specify a time for delivery of care 1210, and a provider or mode of care 1220. However, the patient's visit may be with a different provider 1230, and the care delivered at that time may not be consistent with the triage information. The claims data from the patient visit 1203 includes the diagnosis (ICD-9), the treatment (CPT-2) and the provider (NPIN). The claims data typically does not reflect the P2P relationship, does not permit comparison of the planned care with the care actually delivered, and does not measure the response time. Furthermore, the claims data typically does not provide any of the triage information, and does not point out the P2P relationship except to indicate one instance of care delivery.

Figure 13A:
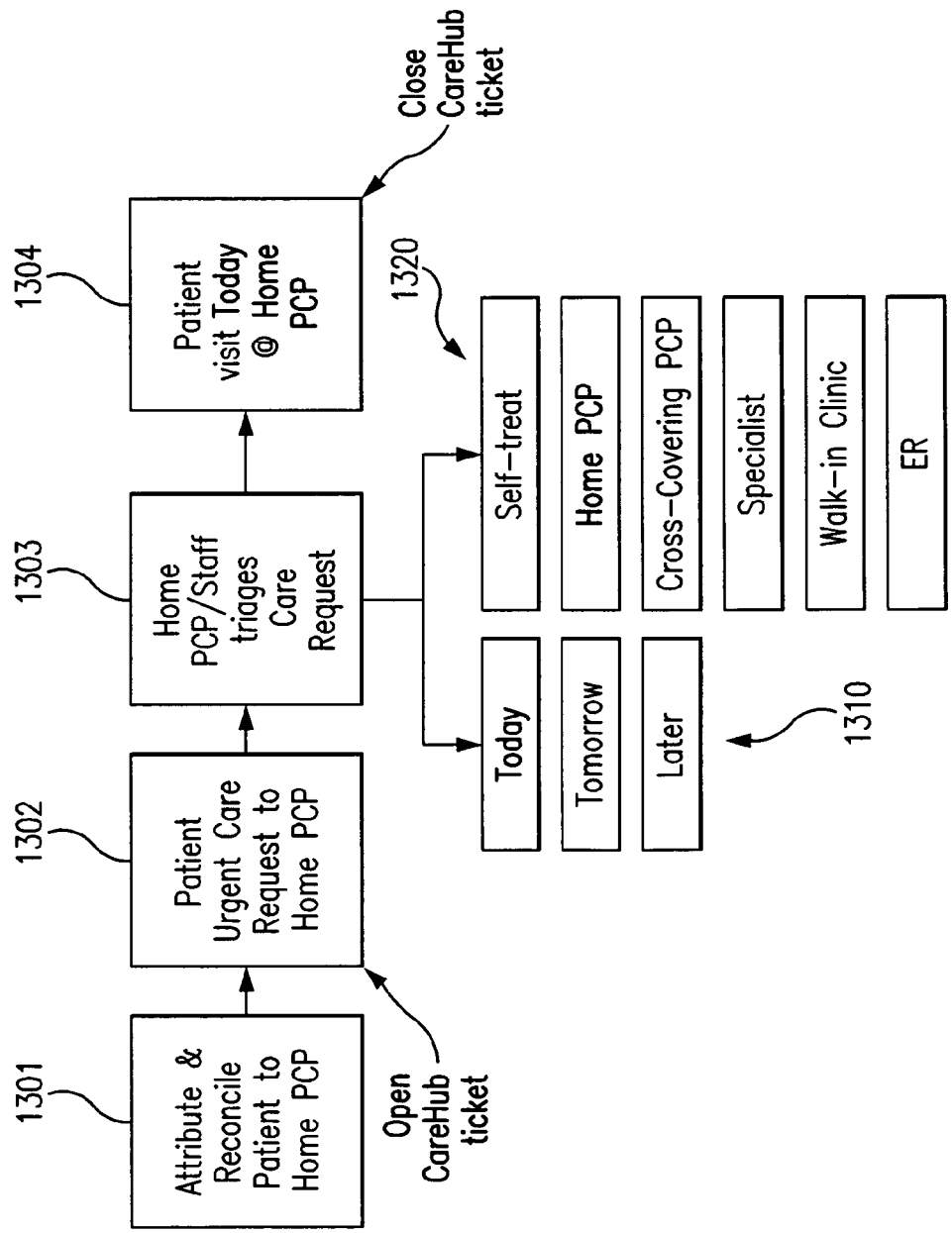
FIGS. 13A and 13B schematically illustrate documentation of urgent care requests, triage, and patient visits using CareHub tickets in accordance with an embodiment of the disclosure.
Figure 13B:
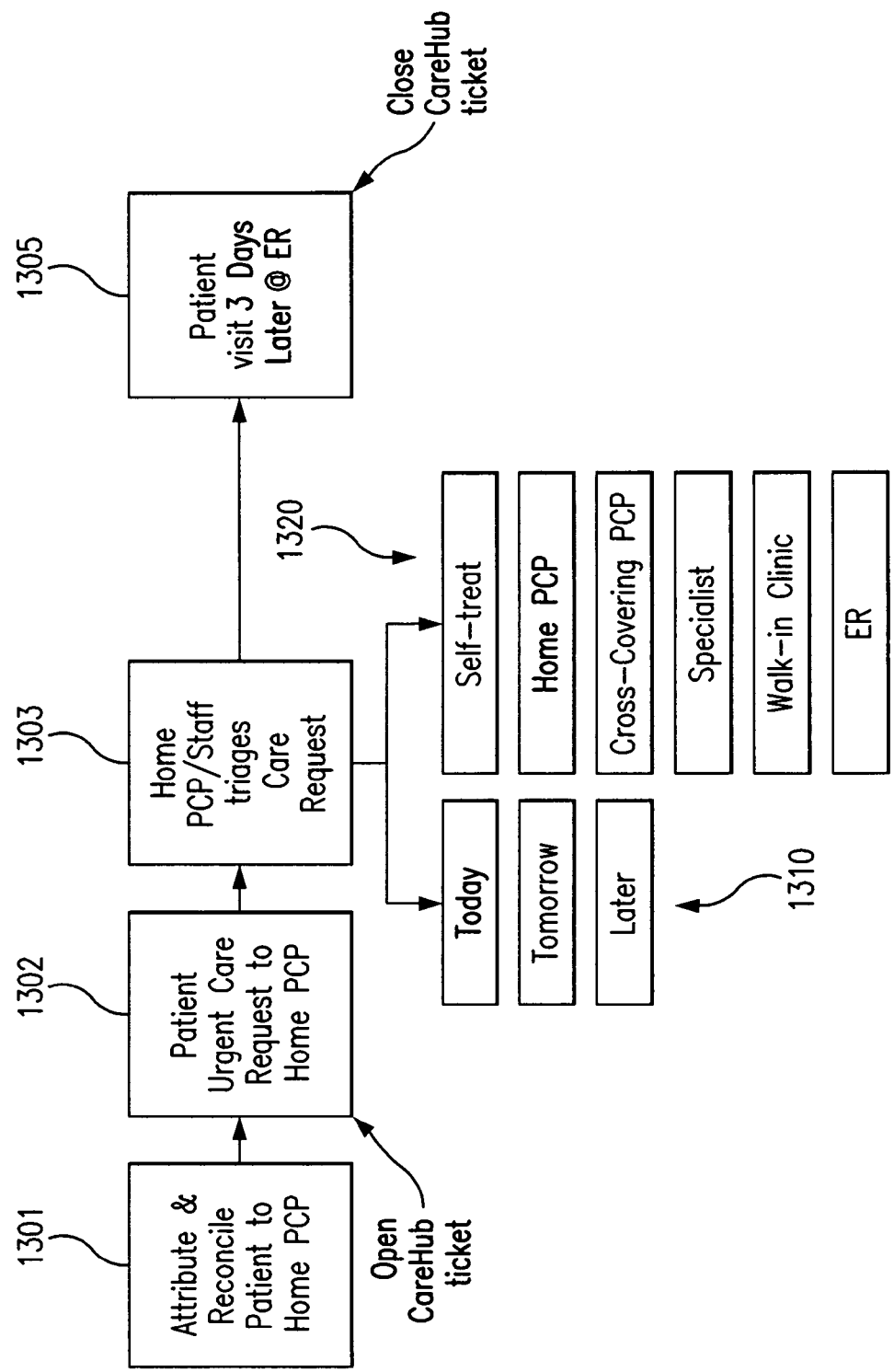

FIGS. 13A and 13B, by contrast, illustrate documentation of an urgent care request using a CareHub ticket. A patient, having a relationship (determined by an attribution/reconciliation process 1301) with a Home PCP, makes an urgent care request 1302 which results in a CareHub ticket being opened. The CareHub ticket is used to document triage of the request 1303, including the planned time for treatment 1310 and the mode/place of treatment 1320. In the example of FIG. 13A, care is delivered according to the plan; the patient visit 1304 occurs the same day as the request, and care is provided by the Home PCP (resulting in the CareHub ticket being closed). The response time, the planned care, the actual care, and the patient-provider relationship are all documented. In the example of FIG. 13B, care is not delivered according to the plan; the patient visit 1305 is three days later and occurs at an ER rather than with the PCP. The longer response time and deviation from the plan are documented. This documentation permits an inference (which typically could not be obtained from the ER claims data) that the ER visit occurred only because the PCP visit did not occur as planned, and thus perhaps was avoidable.

Figure 14:
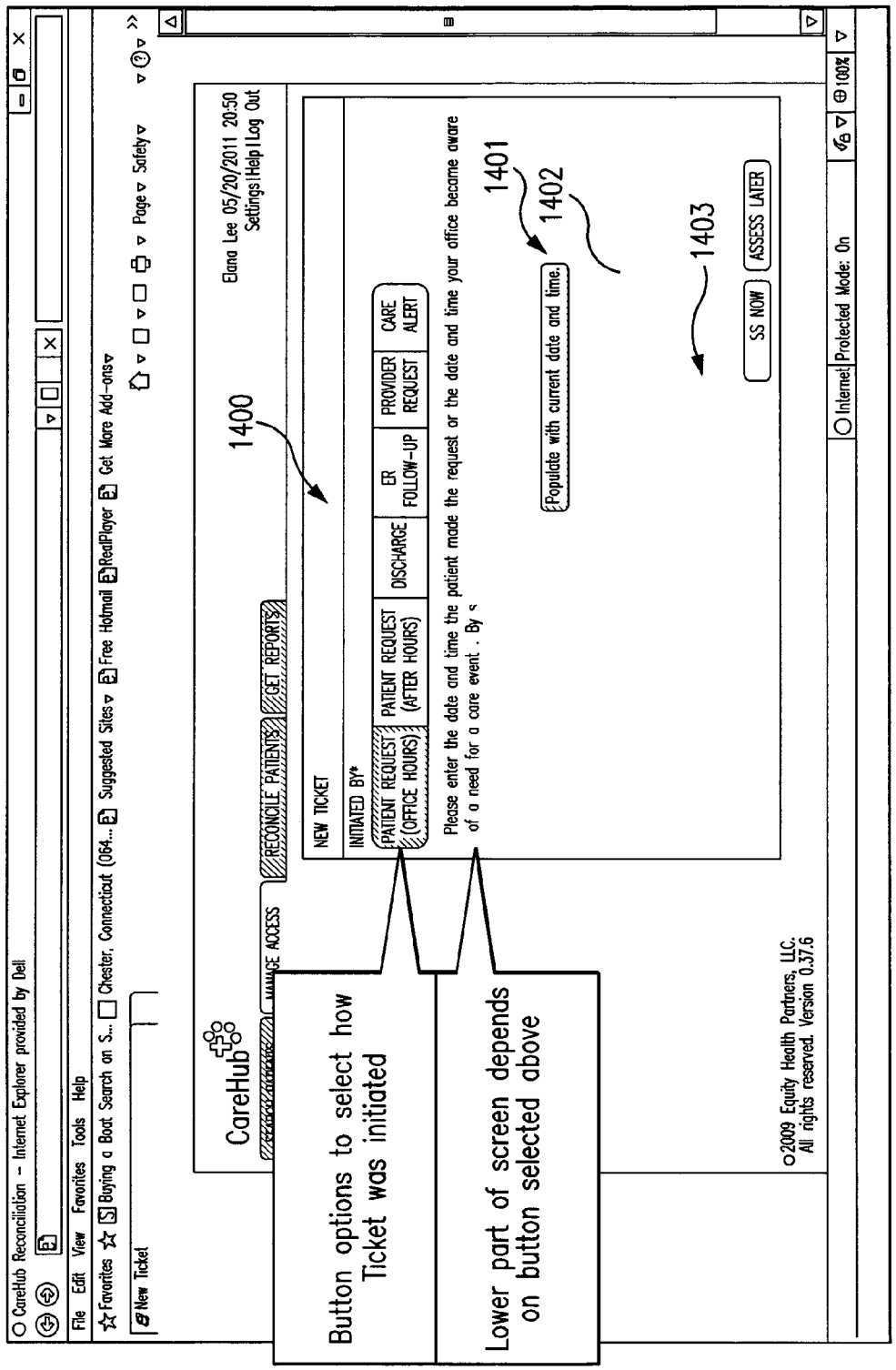
FIG. 14 is a screenshot illustrating an implementation of a procedure for opening a CareHub ticket in the process of FIG. 11.
Figure 15A:
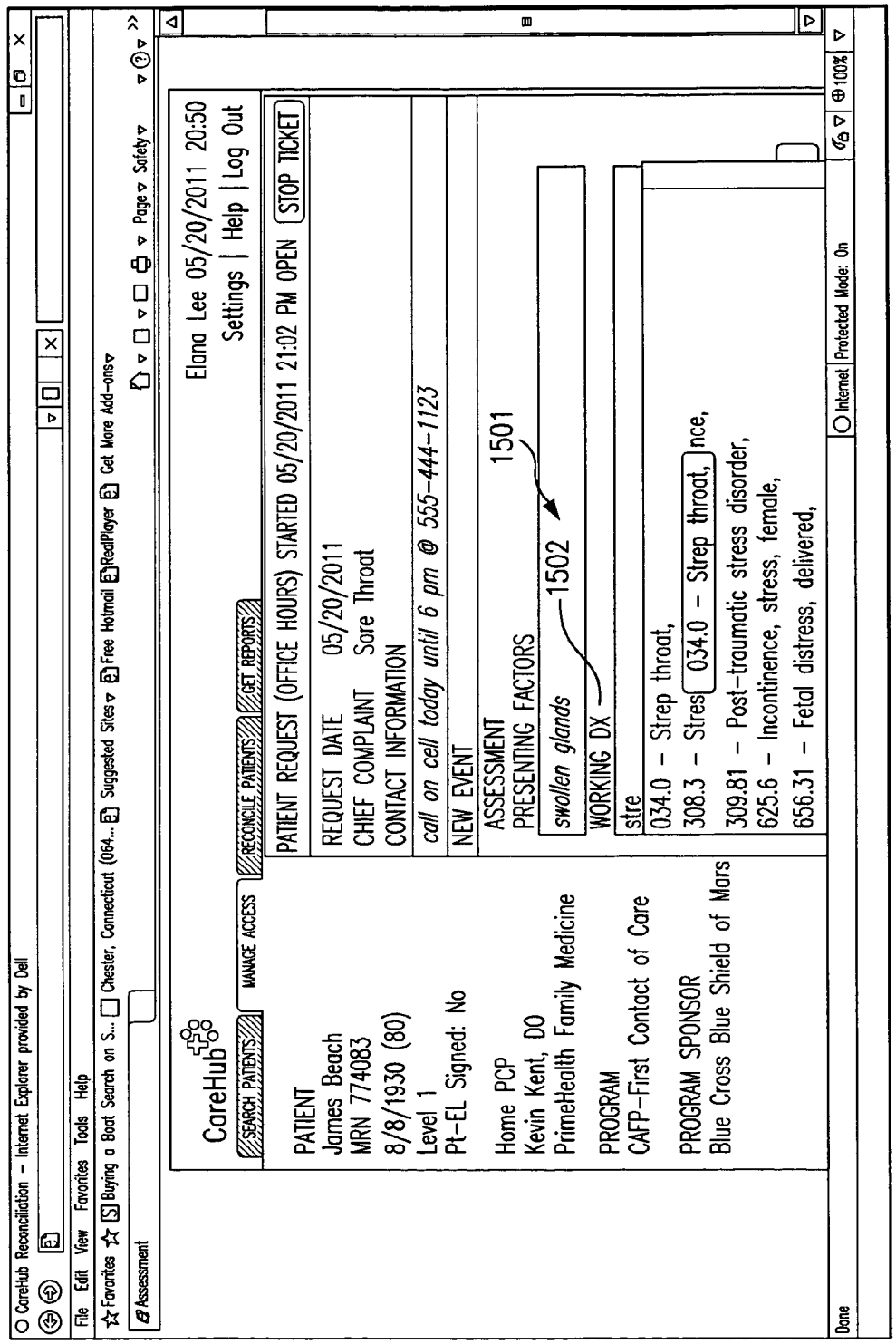
Figure 15B:
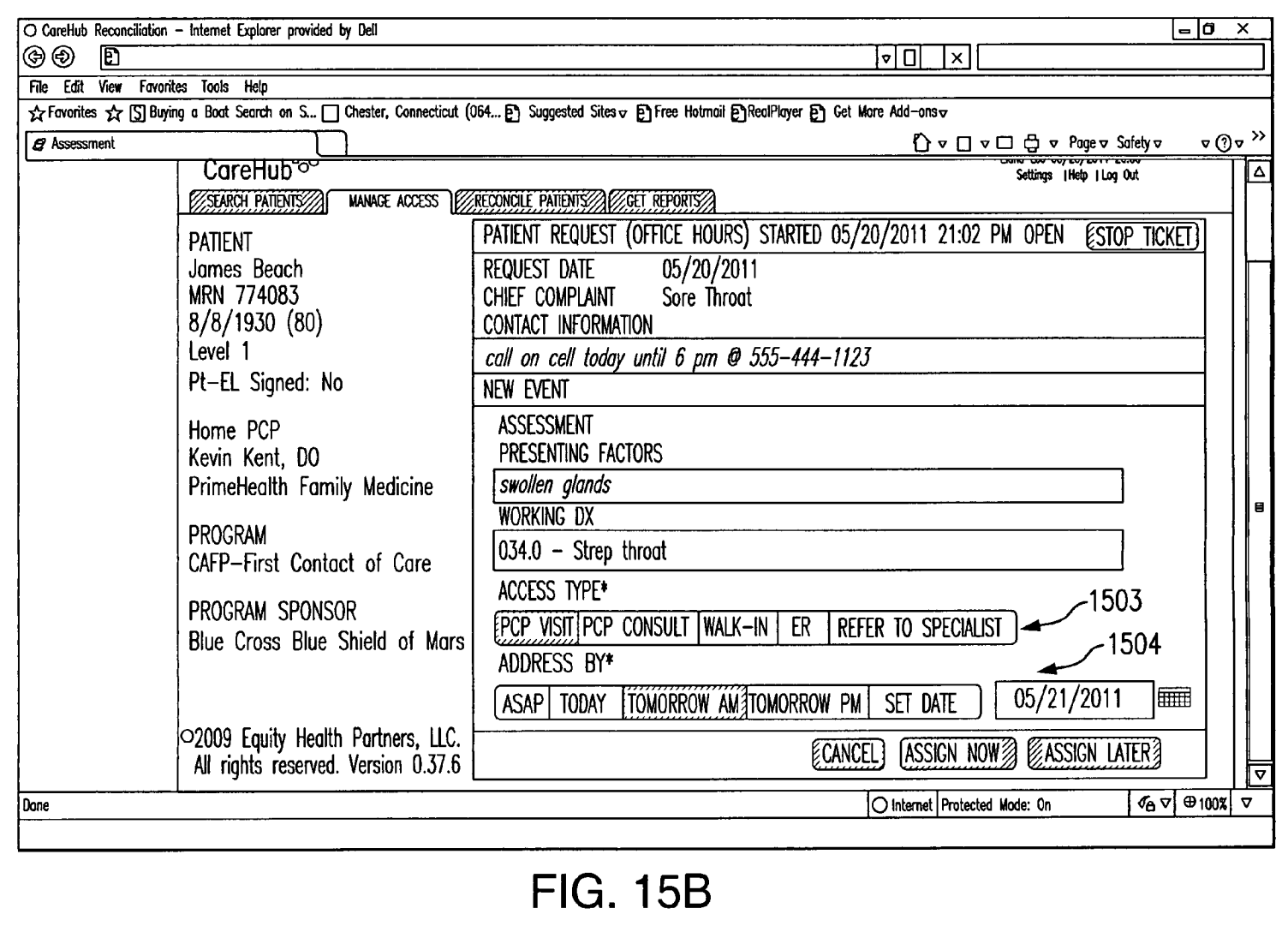

According to an embodiment, the person opening a new ticket 1400 selects how the ticket was initiated from several displayed options (see FIG. 14). Depending on how the ticket was initiated, different types of information may be entered. In this example, the ticket is opened in response to a call from a patient during the PCP's office hours. The date and time 1401 of the request are noted, along with the patient's complaint 1402 and contact information 1403. FIGS. 15A and 15B illustrate assessment of the care request in this embodiment. The patient's presenting factors 1501 are entered below the request data, and a working diagnosis 1502 is selected. As shown in FIG. 15A, the "Working DX" may be selected from a menu that is displayed in response to a few keystrokes (in this example, keying "stre" causes display of a menu with "strep throat" at the head of the list, along with the appropriate CPT-2 code). A decision on how to provide treatment is then entered at 1503, e.g. a planned patient visit to the PCP. From the provider's point of view, this is referred to as managing the patient's "access to care." The planned time for providing care is entered at 1504.

Figure 16:
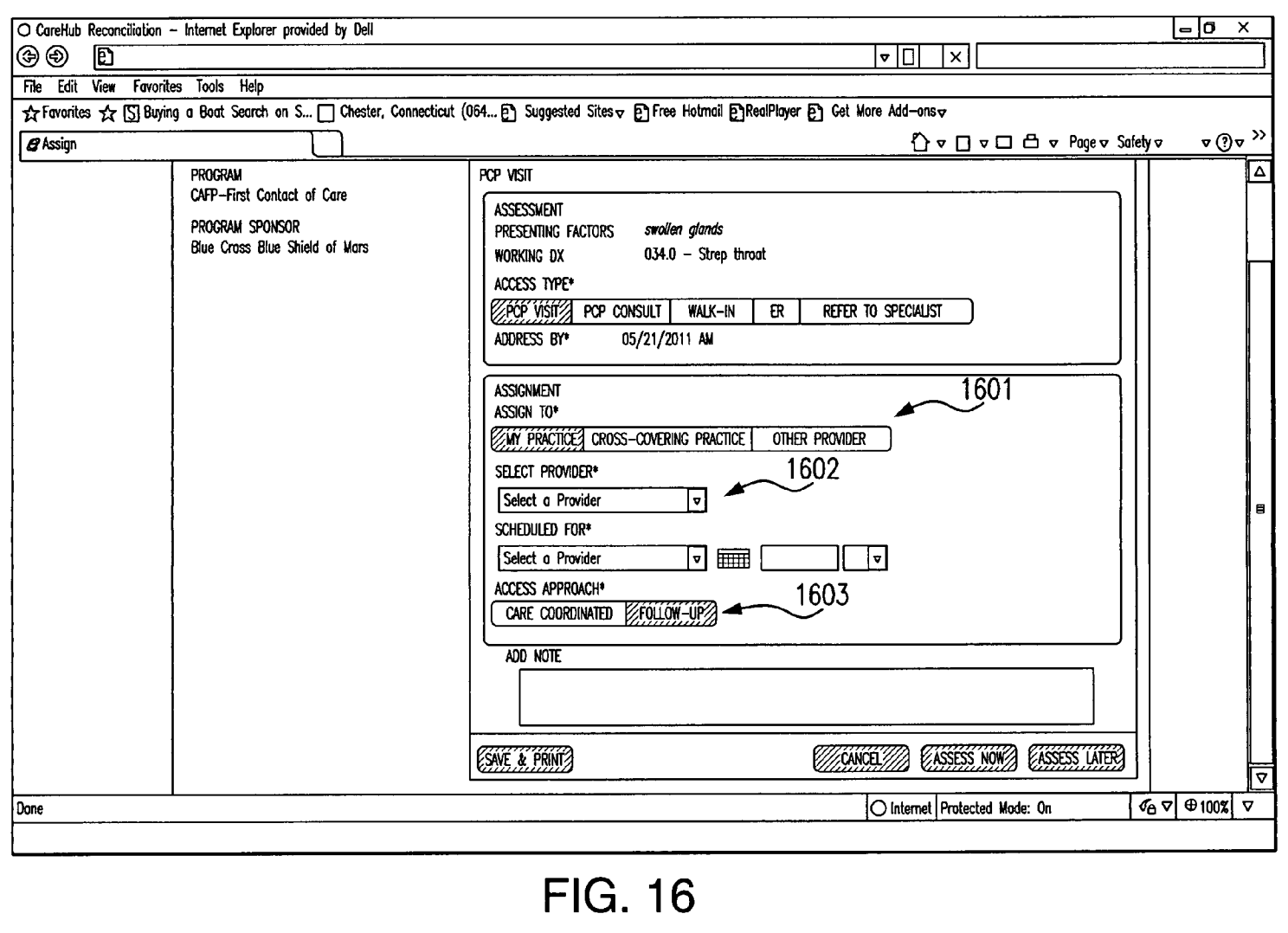

Information regarding the provider who is to deliver the planned care is entered below the "Assignment" label (FIG. 16). In this embodiment, the assignment 1601 is to either the PCP's own practice, a cross-covering practice, or another provider. A particular provider is selected using a menu 1602. A selection 1603 then is made whether care is to be coordinated with another provider, or follow-up will be performed by the PCP.

Figure 17:
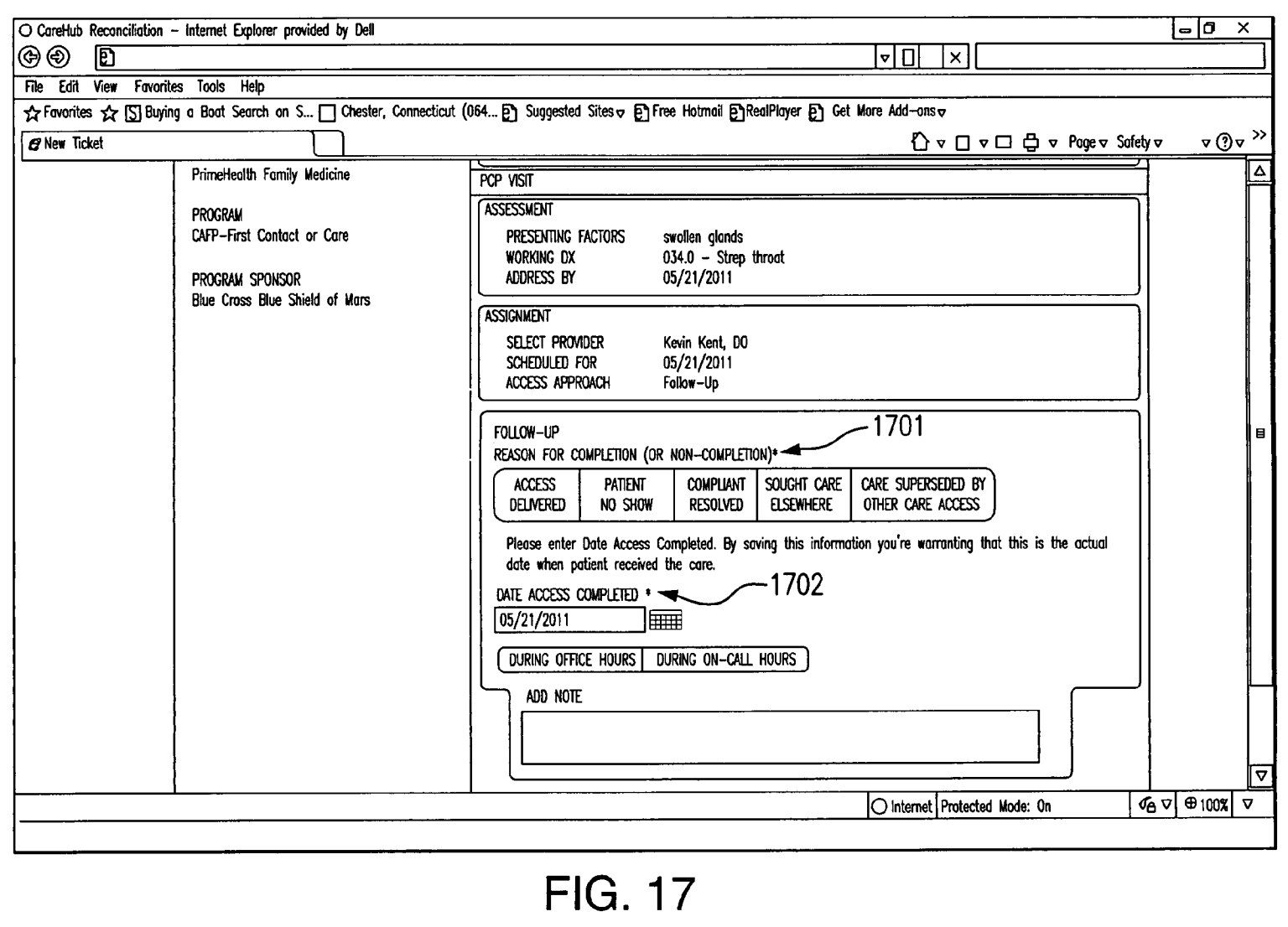

Follow-up information is entered below the assignment (FIG. 17). The reason for completion of the access to care (e.g. treatment was provided), or non-completion, is documented. The date 1702 that access to care was completed is also documented; this should be the date when the patient actually received care.

Figure 18A:
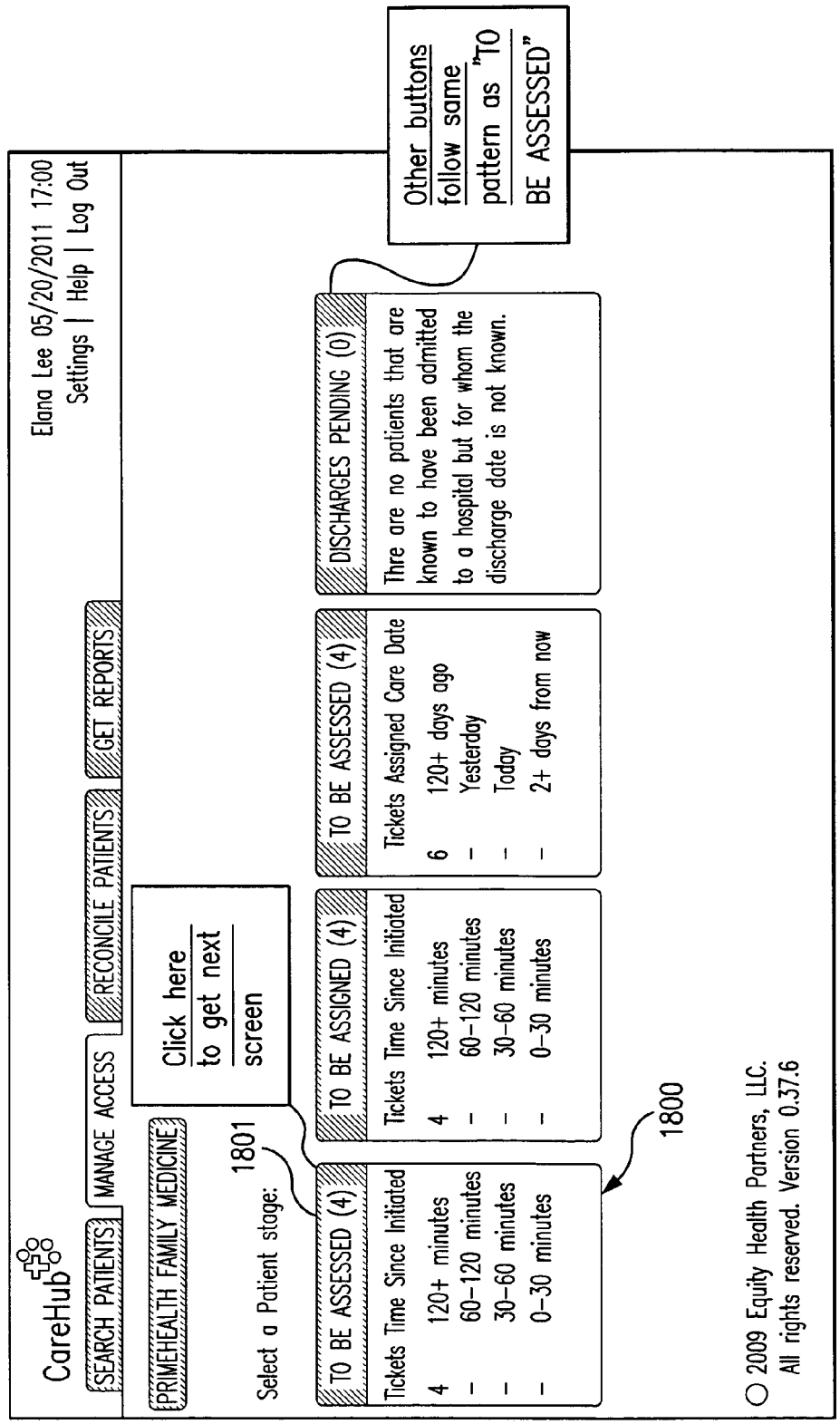
Figure 19A:
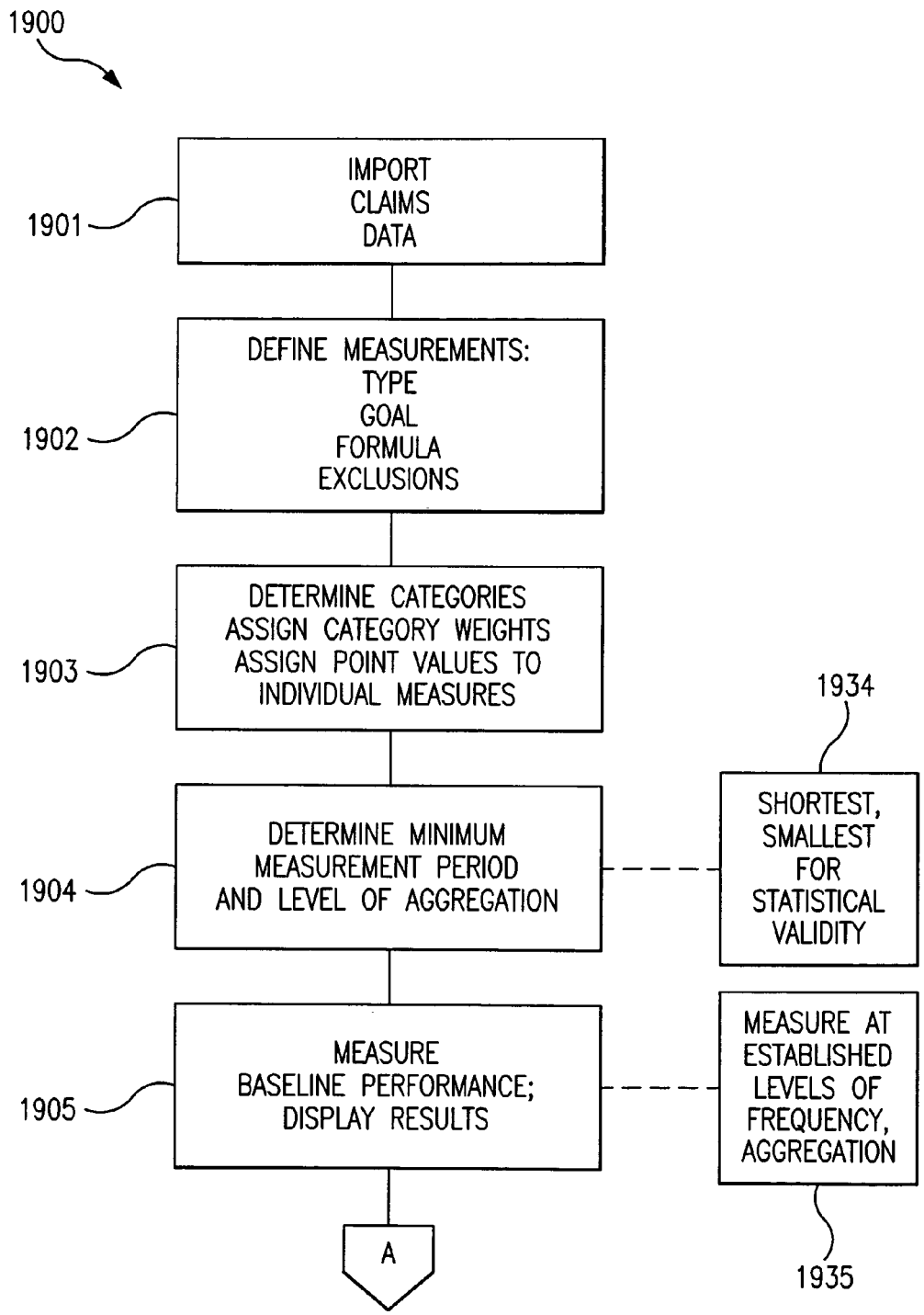
FIGS. 19A-19D are connected flowcharts showing further details of a performance measurement and reward calculation procedure according to an embodiment of the disclosure.
Figure 19B:
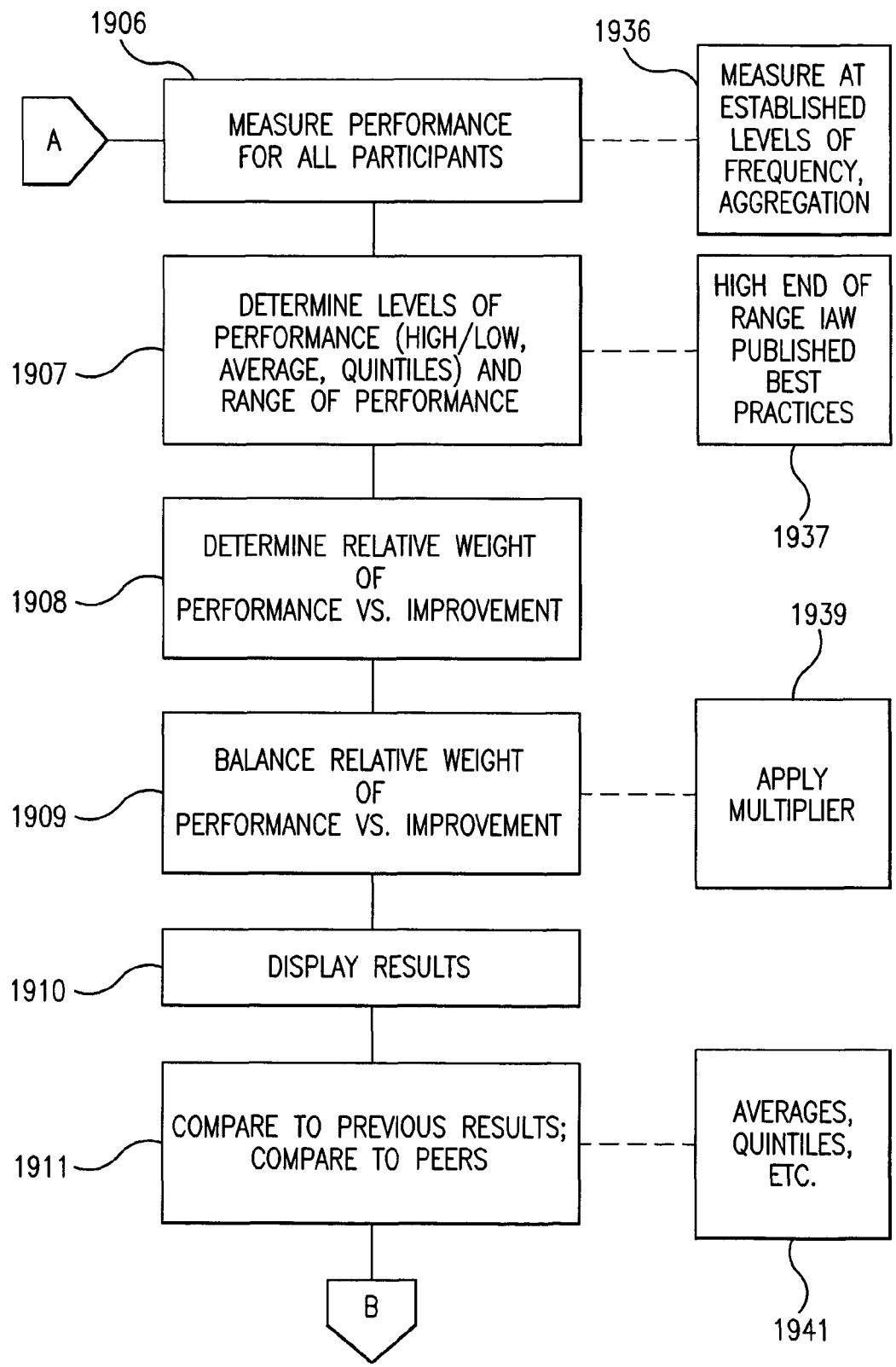
Figure 19C:
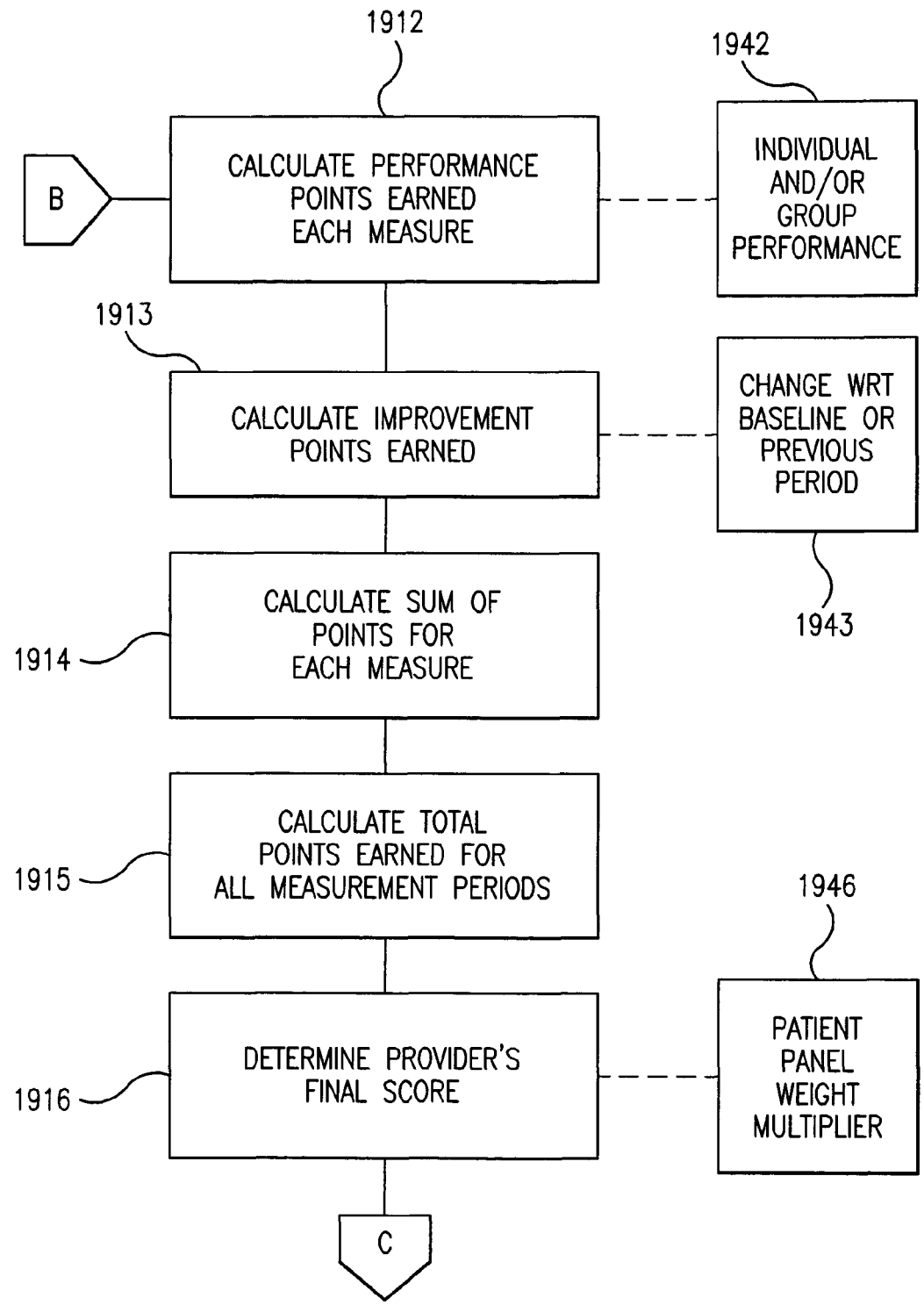
Figure 19D:
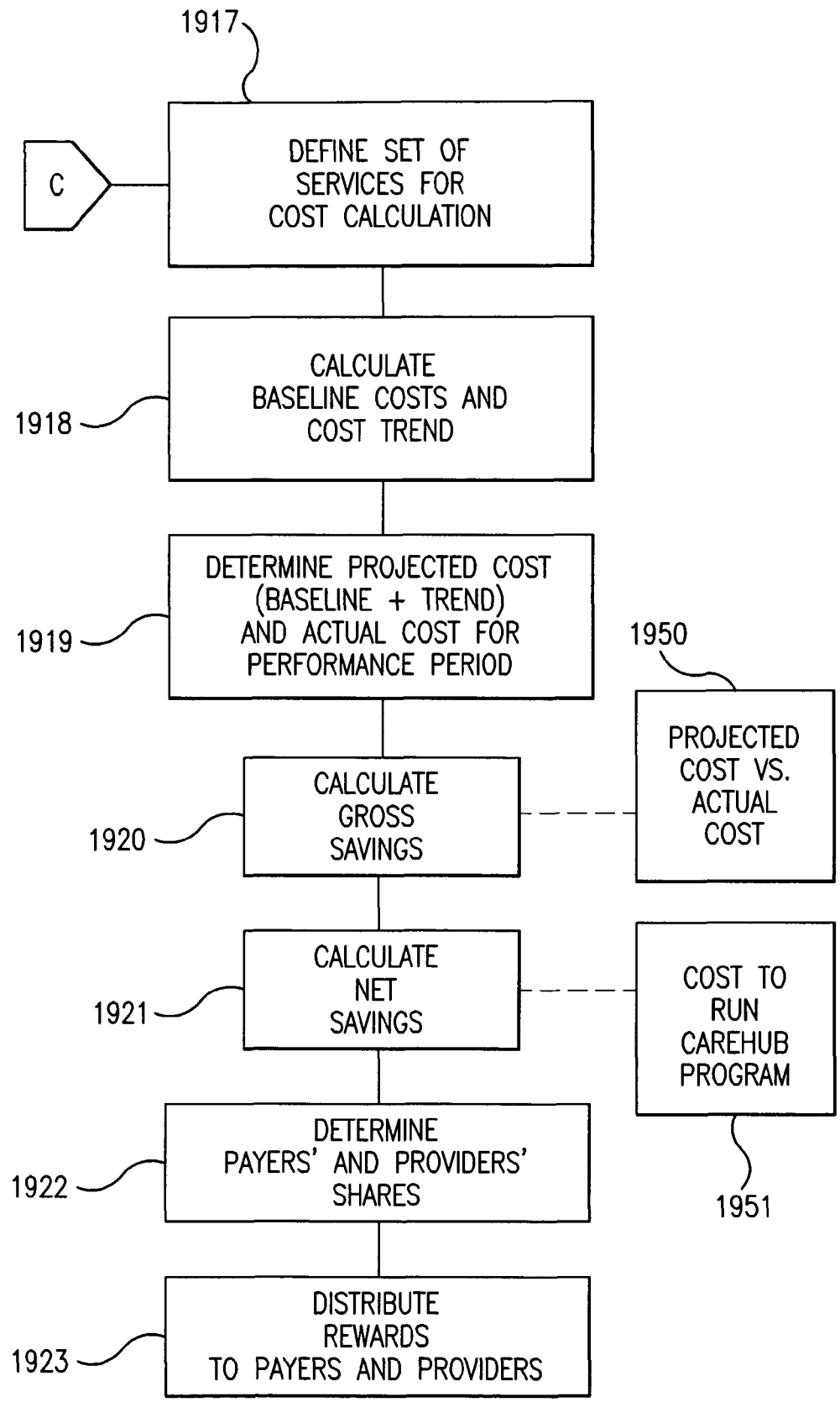

In an embodiment, the tracking module may also present summaries regarding management of patients' access to care, as shown in FIGS. 18A-18C. For example, in FIG. 18A, a summary 1800 shows that four tickets are awaiting assessment, with those four tickets initiated more than 120 minutes previously. Clicking on the "to be assessed" header 1801 causes details 1802 of those tickets to be displayed (FIG. 18B), including the name of the patient and the name of the patient's Home PCP. Clicking on a particular patient's name causes display of the fields for entering assessment data (FIG. 18C). Assessment data for that patient may now be entered as discussed with reference to FIG. 15B. Summary 1800 may similarly show the number of tickets awaiting assignment to a provider, for which a hospital discharge is pending or has occurred, etc.

Performance Measurements, Analysis and Rewards

In an embodiment of the disclosure, the performance of providers is measured and analyzed by the Analysis and Rewards module 13. In this embodiment, both performance and improvement are measured and rewarded, so as to encourage improvement and sustained high performance. The analysis and reward system also is designed to reduce or eliminate unintended consequences (such as over-emphasizing access to care, and thereby disrupting continuity-of-care) and to reduce or eliminate gaming (fraudulent data entry).

Some criteria by which performance may be measured are listed in Table 1:

uses a combination of data entered into CareHub and claims data imported from the payer's database (step 1901). Each measurement criterion is defined (step 1902) with some basic characteristics: the type of measurement (e.g. response time), the standard or goal for the measurement (e.g. "response within two days"), the formula for quantifying performance (e.g. "all urgent care requests fulfilled within two days" divided by "all urgent care requests"), and possible exclusions (e.g. "do not include events after patient opt-out date").

In step 1903, measurements are sorted into one or more categories, e.g. "access and continuity," "physician engagement," "hospital discharge management," etc. These categories are assigned weights based on their relative importance with respect to financial, clinical or other concerns. Point values are then assigned to individual measures within a category. For example, if "access and continuity" is deemed to have 50% of the total weight of the above-noted three categories (or 500 points out of a total of 1000), then individual measurements in that category might have different point values as follows:

Access to care within two days: 300 points
Continuity with the Home PCP: 100 points
Continuity with the Home PCP's practice: 75 points
Continuity with the Home FQHC (a group of practices): 25 points The frequency and level of aggregation is then determined for each measurement (step 1904). Measurements are made with the shortest measurement period and lowest level of aggregation 1934 required for statistical validity. For example, where the level of aggregation is a single PCP and measurements are performed monthly, if the number is less than the statistical minimum (usually N=30) the measurement may be performed less often (quarterly or annually) or at a higher level of aggregation (the PCP's practice, or a cohort of PCPs). Measurements of performance are made (step 1905) at the established levels of frequency and aggregation 1935, to establish a baseline. In this embodiment, the results are displayed as well as stored for later comparisons.

Measurements of performance are then made for all participants (step 1906) at the established levels of frequency and aggregation 1936. Levels of performance are determined

TABLE 1

| Name | Frequency | Definition | Notes |
| --- | --- | --- | --- |
| Access | Quarterly | % of Urgent Care Requests fulfilled within 2 business days | Measures "Access to Care" |
| Continuity | Quarterly | % of Urgent Care Requests fulfilled by HomePCP or HomePractice | Counter-balancing measure to "Access" designed to promote Continuity of Care |
| ER with CareHub Ticket | Quarterly | % of Emergency Room visits with CareHub tracking ticket | Indicates degree to which Urgent Care Requests are being logged by PCP, and whether Patients call HomePCP as First Contact for Care |
| High Risk Patients | Quarterly | % of High Risk Patients with whom there is a "Patient-to-PCP Agreement" to use HomePCP for First Contact of Care | "High Risk" = Patients with a higher tendency to need or seek care |
| Attendance at Cohort Meetings | Quarterly | % of monthly Cohort Meetings (peer learning sessions) attended | To engage PCPs in the program and with each other |
| Non-Emergent Care at ER | Annually | % of Non-Emergent services treated in Emergency Room | Uses a set of ICD-9 codes (ICD = International Classification of Diagnosis) to identify Non-Emergent care |
| Discharge Follow-UP | Annually | % of Patients discharged from Hospital With a PCP follow-up visit within 7 days | To encourage care coordination and reduce re-admissions |

A process 1900 for measuring and rewarding provider performance and improvement, according to an embodiment of the disclosure, is shown in FIGS. 19A-19D. The module from the measurement results (step 1907); for example, highest, lowest, average, and quintiles. The measured range of performance (highest to lowest) is taken as a tentative range of improvement. A measurement may have a "best practices" level as reported in the professional literature. If this level is higher than the highest level actually measured, then the upper end of the range of performance may be revised upward in accordance with the published best practices (step 1937). The relative weight of performance vs. improvement is determined (step 1908). It is desirable to balance performance and improvement (step 1909) to encourage improvement, without discouraging excellent performance; accordingly, in this embodiment performance and improvement are given equal weight; that is, point scores for performance and improvement each are given a multiplier (step 1939) of 50%.

Performance scores may similarly be balanced between individuals and groups. For example, if in a multi-person practice group the group's efforts are considered to be as important as each individual's, individual and group measurements will be given equal weight when calculating the point score for a given individual.

The results are displayed (step 1910) and then analyzed. For example, both peer-to-peer comparisons and month-to-month comparisons may be made (step 1911). Each group of results may have averages, quintiles, etc. calculated (step 1941). Where performance is based partly on an individual's effort and partly on a group's effort, a multiplier may be determined which is then applied to the performance points for that measurement. Performance points are calculated for each individual and group for each measurement criterion (steps 1912, 1942), and improvement points are calculated (step 1913) with the multiplier from step 1939. Improvement may be measured as change with respect to a baseline or with respect to performance in a previous period (step 1943).

For each provider, the sum of points for each measure is determined (step 1914) and the total of points is calculated (step 1915) for all the measurement periods in the rewards period (e.g. where monthly or quarterly measurements are made, while rewards are calculated annually).

Since the various providers have different numbers of patients, and the number of patients for a given provider fluctuates throughout the rewards period, a "patient panel weight" multiplier is applied to the provider's point total. The number of patient months for the provider (one patient month being one patient being enrolled in the care program for one month) is divided by a constant factor. The provider's final score is determined (step 1916) after applying the patient panel multiplier 1946.

Rewards may be based on financial savings due to quality performance and/or reduction in the cost of services. In this embodiment, rewards are distributed as shares of net savings derived from operating the care program with CareHub. A set of services is defined whose costs are to be measured (step 1917); e.g. the cost of ER visits. A calculation is made (step 1918) of baseline costs (that is, costs of the services for a given prior period, usually one year) and the cost trend (e.g. increase in costs year-over-year). From the baseline cost and cost trend data, a projected cost is determined (step 1919); the actual cost for the time period of interest is also determined. A comparison of these costs (steps 1920, 1950) yields the gross savings.

The cost to run the care program is calculated (step 1951); this cost typically includes the Care Management amount (per member per month, or $pmpm) paid to providers, and fees directly related to operating CareHub. The net savings is calculated (step 1921) as the difference between gross savings and this figure. The payers' and providers' respective shares are determined (step 1922) in accordance with prior agreements between the various parties. The shared savings are distributed as rewards (step 1923) to the payers and providers.

Figure 20:
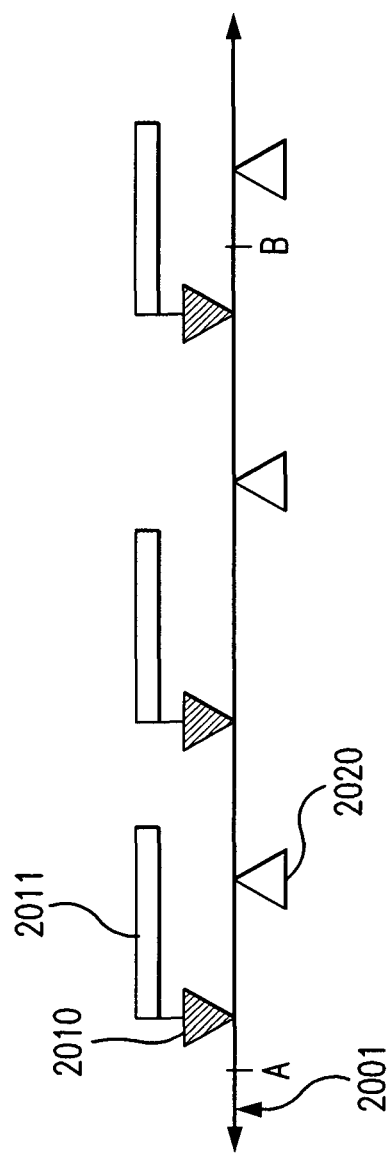
FIG. 20 illustrates a timeline with discharge and followup events marked thereon, illustrating part of a performance measurement in the process of FIGS. 19A-19D.
Figure 21:
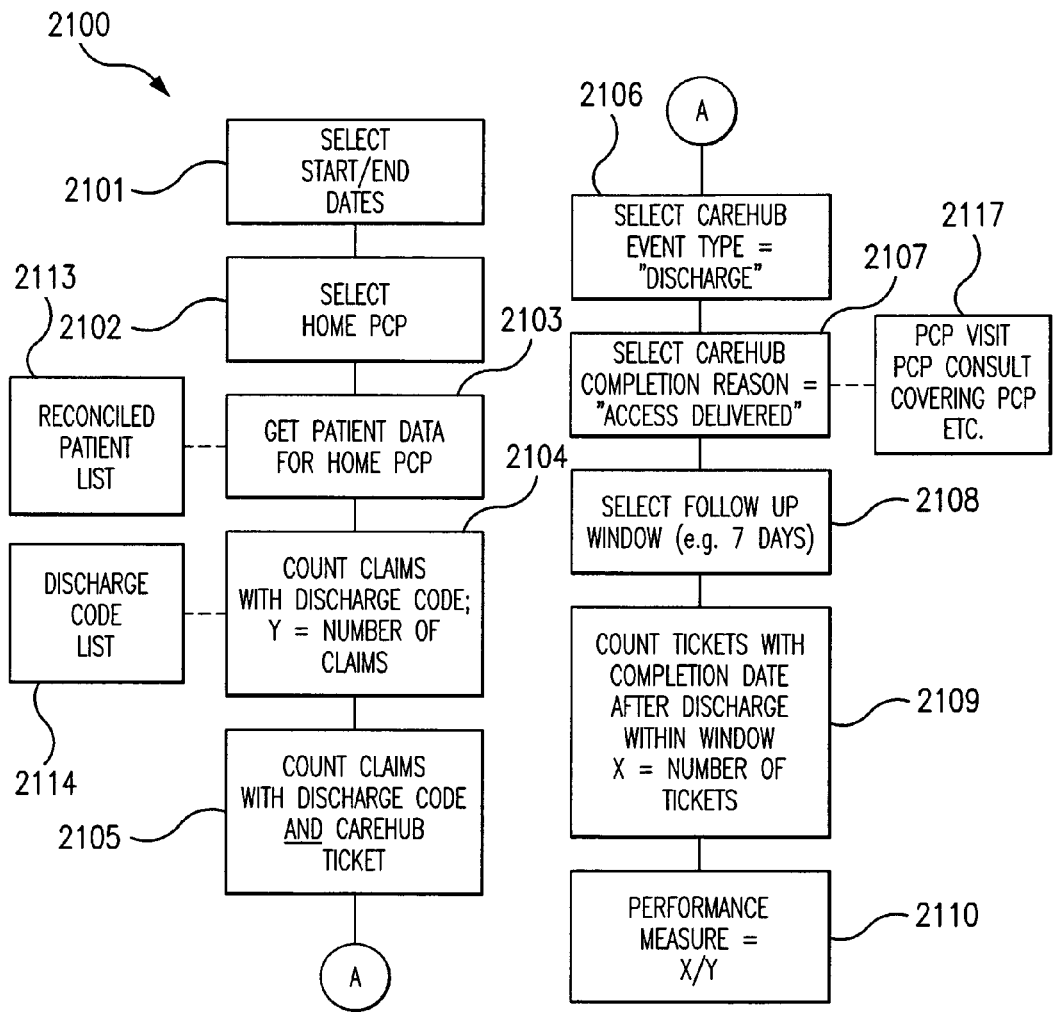
FIG. 21 is a flowchart showing steps in a procedure for measuring performance relating to followup after patient discharge, according to an embodiment of the disclosure.

Calculation of a specific performance measurement, according to an embodiment of the disclosure, is shown in FIGS. 20 and 21. The measurement is defined as "number of patients seen by the Home PCP within 7 days of hospital discharge." The measurement period is one month. FIG. 20 schematically illustrates a reporting month with a timeline 2001; the month begins at A and ends at B. Hospital discharges of the Home PCP's patients during the month occur at points 2010, with a seven-day window 2011; the PCP's follow-ups to those discharges occur at 2020. As shown in FIG. 20, three hospital discharges 2010 occurred during the month. One follow-up event 2020 was within window 2011; one was outside the window; one was within the window but not during the reporting month. Thus an accurate report would show that 50% of the follow-ups in the month met the stated criterion, with one "discharge pending follow-up."

FIG. 21 shows a flowchart with a procedure 2100 for calculating provider performance for this criterion. It is noteworthy that the data used is a combination of CareHub data and claims data. The starting and ending dates for the reporting period are selected (step 2101); in this case, "date of discharge"=first and last dates of the month of interest. The Home PCP whose performance is to be measured is selected (step 2102). Data for the Home PCP's patients is retrieved (step 2103); these patients appear on the provider's reconciled patient list 2113. In step 2104, the number of claims is counted where a patient in this list is associated with a code indicating a hospital discharge (a code on discharge code list 2114). This number of claims is assigned to variable Y.

A follow-up by the Home PCP should be reflected in a CareHub ticket. Accordingly, the number of claims is counted (step 2105) where there is both a discharge code and a CareHub ticket. The CareHub system then selects the tickets where the event type is "discharge" (step 2106), and where the access to care is complete, with the completion reason being "access delivered" (step 2107). The access to care may have been delivered in the form of a PCP visit, a PCP consult, a visit with a covering PCP, etc. (step 2117). A window of time (in this case, 7 days) is selected for counting CareHub tickets (step 2108). The number of tickets where access to care was completed within the selected window is assigned to variable X (step 2109). The performance measure is then calculated (step 2110) as X/Y.

Figure 22:
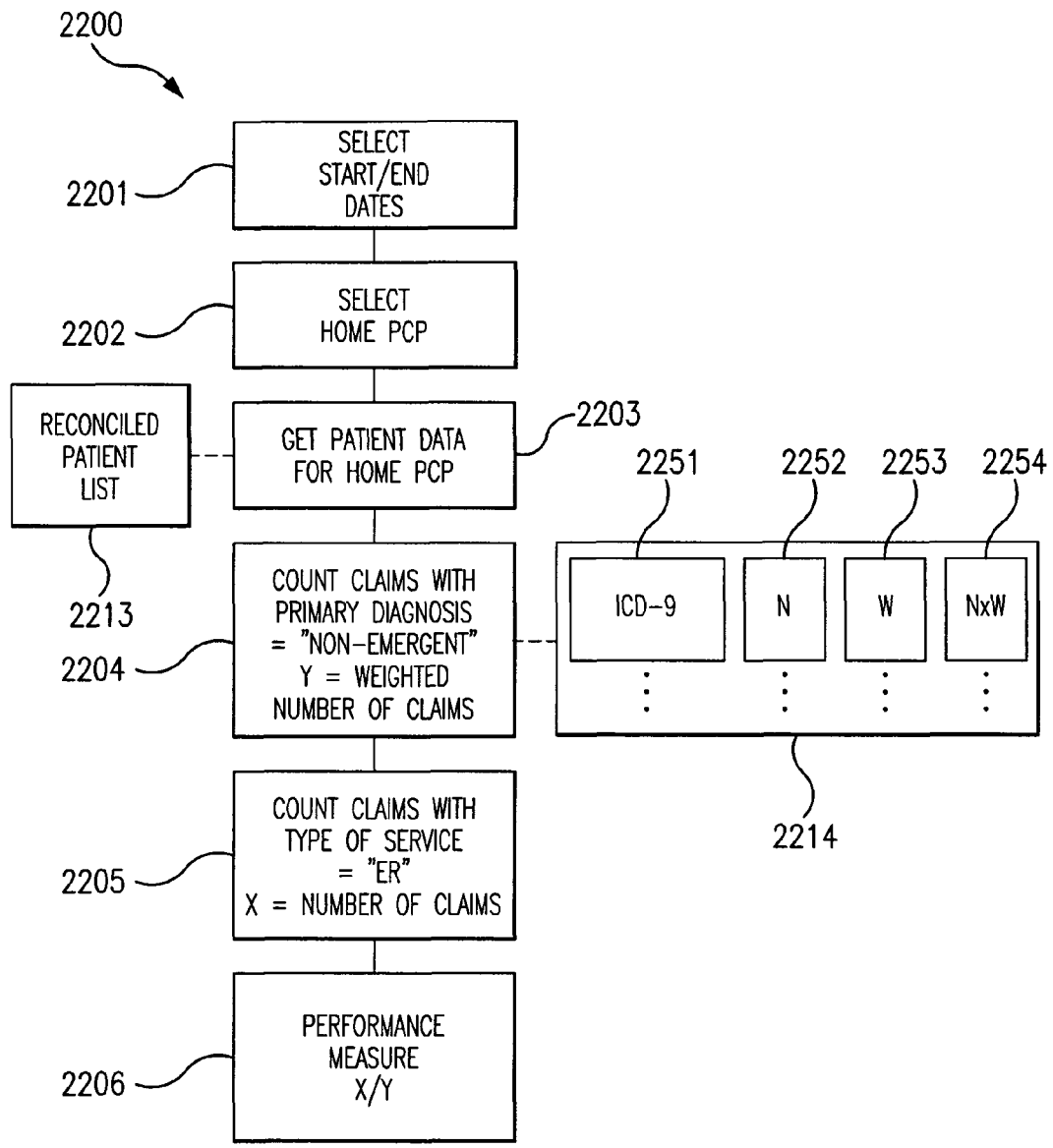
FIG. 22 is a flowchart showing steps in a procedure for measuring performance relating to diagnoses of a non-emergent condition, according to an embodiment of the disclosure.

Another example of a performance measurement, shown in FIG. 22, is a procedure 2200 for determining the proportion of non-emergent care events treated at an emergency room. The start and end dates are selected (step 2201), the Home PCP is selected (step 2202), and the patient data for the Home PCP is retrieved (step 2203) in accordance with the reconciled patient list 2213, as described above. The number of claims is counted (step 2204) where the primary diagnosis is "non-emergent." This number is weighted (step 2214) according to the ICD-9 codes 2251 accompanying the non-emergent diagnosis. This is done to take into account the proportion of cases that should be treated in the ER, based on the particular ICD-9 code. The number of cases 2252 with such codes is multiplied by a weighting factor 2253 to yield a total 2254, which is used as an effective number of non-emergent claims. This number is assigned to variable Y. The number of CareHub tickets is counted (step 2205) where the type of service was "ER" for the reporting period; this number is assigned to variable X. The performance measure is then calculated (step 2206) as X/Y.

Figure 23A:
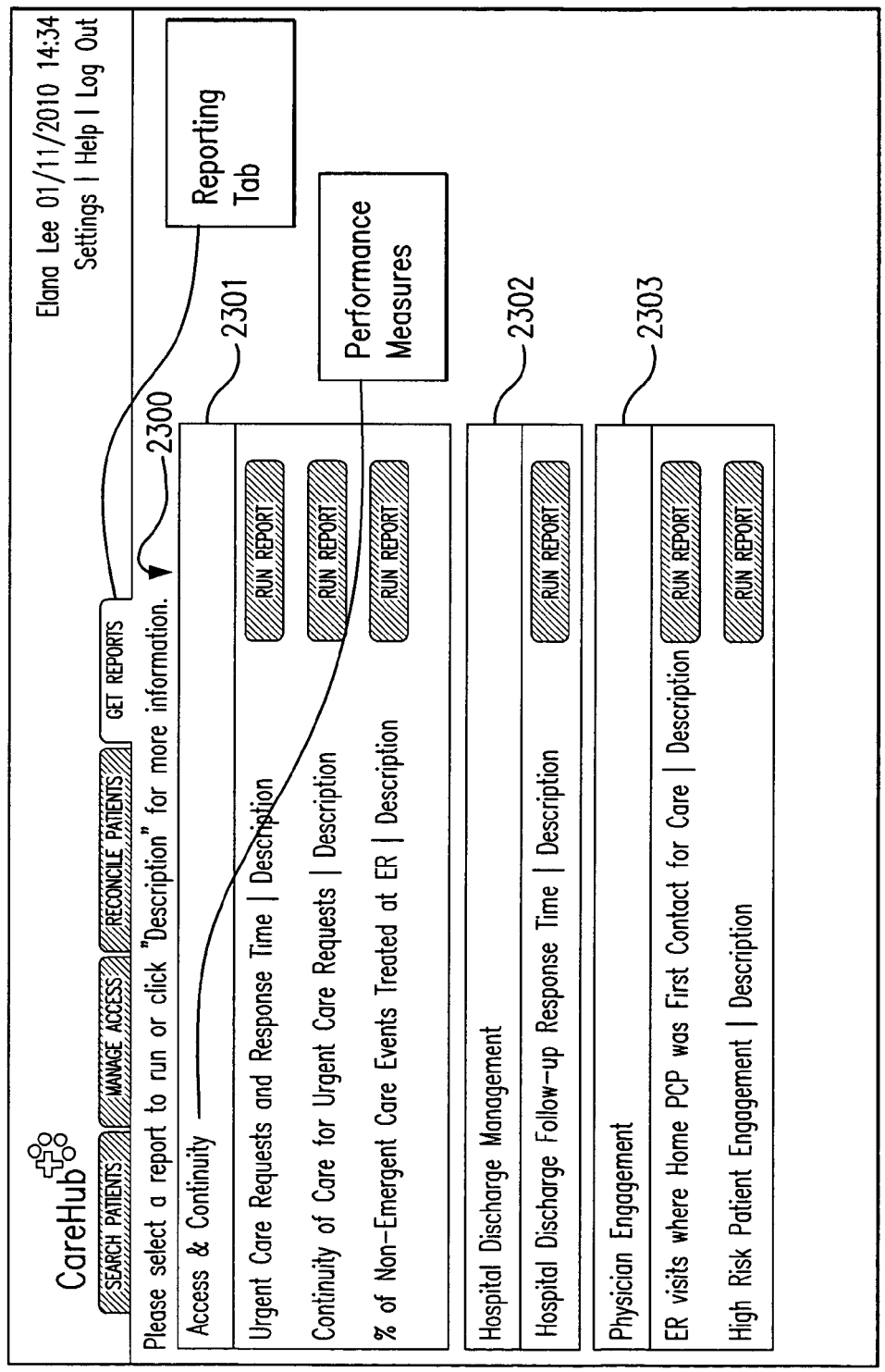
Figure 23B:
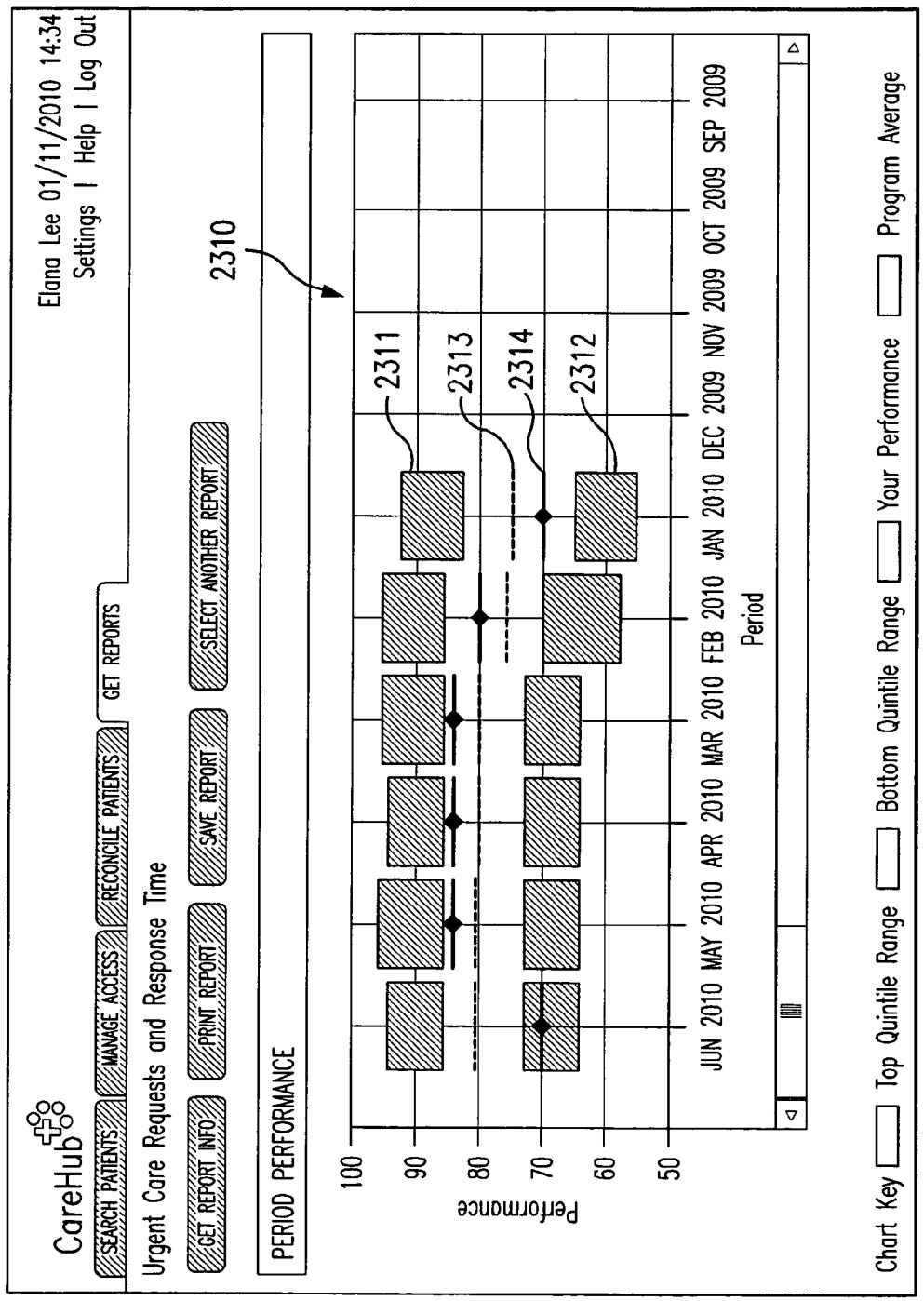

Further examples of reports that may be generated using CareHub, in accordance with embodiments of the disclosure, are shown in FIGS. 23A-23E. FIG. 23A shows a list 2300 of available reports, related to performance measurements in three broad categories: "Access and Continuity" 2301, "Hospital Discharge Management" 2302, and "Physician Engagement" 2303. Selecting one report in this list ("Urgent Care Requests and Response Time") causes the report to be displayed, as shown in FIG. 23B. The report 2310 shows performance measurements on a monthly basis, expressed in terms of the percentage of urgent care requests where the response time criterion was met. For each month, the top and bottom quintiles 2311, 2312 and the average performance 2313 are shown. A provider can instantly compare his/her own performance 2314 with the performance of the cohort of providers. Numeric data 2320 for each month are displayed below the graph, as shown in FIG. 23C.

Figure 23D:
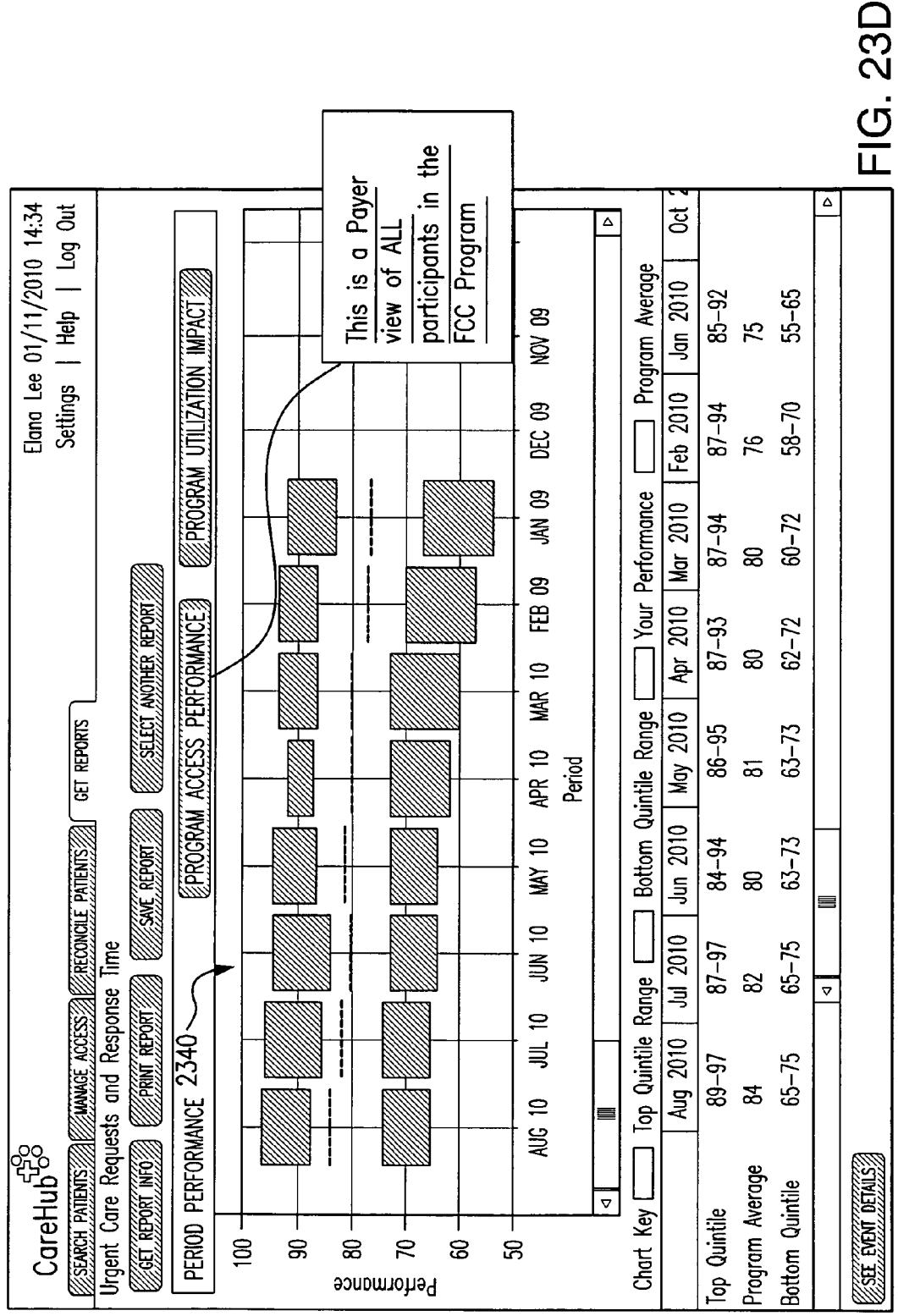

A payer typically is also interested in the performance of all the providers over a period of time, as opposed to comparing one provider's performance with that of a group. A report prepared for a payer is shown in FIG. 23D. Report 2340 shows performance of all participants in the care program for a selected period of months, again relating to the measurement "Urgent Care Requests and Response Time." The payer can instantly view the month-over-month change in the average performance and the top and bottom quintiles.

Figure 23E:
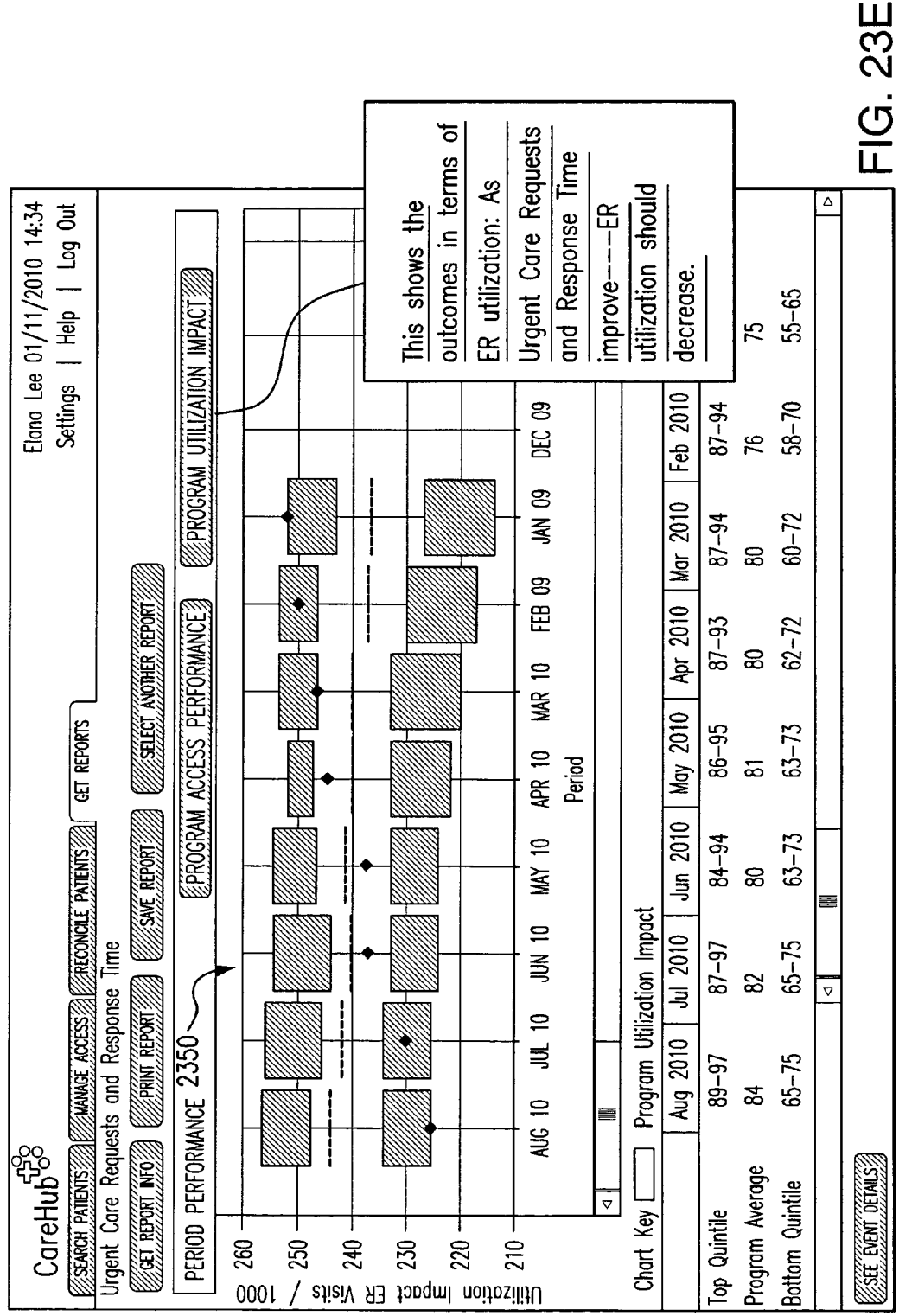

A different type of report, such as shown in FIG. 23E, relates the measured performance to another outcome of interest; in this case, report 2350 shows the relationship between the response time for urgent care requests and emergency room utilization. The horizontal line in each month represents the average response time performance (compare FIG. 23D), while the diamond shape indicates ER utilization in that month. Graph 2350 shows that as the response time for urgent care requests improves, ER utilization decreases.

It will be appreciated that the CareHub performance measurement system can provide answers to important questions that arise in care programs emphasizing access to care, continuity of care, and coordination of care ("A-C-C"). In one such program, "First Contact for Care" (FCC), A-C-C measurements are expected to become critical management tools as insurance coverage expands and Medical Home programs roll out in an already under-supplied primary care system. In particular, CareHub addresses these issues:

Did the Patient use their Medical Home—or go elsewhere? (Measure the percentage of PCP/Specialist/ER visits where the HomePCP was the First Contact for Care)

Are PCPs actually providing access as required of a Medical Home? (Measure urgent care request and response time (i.e. "Access to Care"; same day, next, or later)

Was care provided by the HomePCP, a cross-covering PCP, a Walk-in clinic, or the ER? (Measure continuity of care with HomePCP, or other provider)

Is care coordinated between the PCP and the local hospital? (Measure the percentage of ER and hospital discharges with PCP follow-up within 7 days)

CareHub also addresses a recognized problem with P4P and PCMH home programs, namely that results are only calculated annually (usually 3 to 6 months after year-end to allow for the settling of claims) so that data is of limited value because it is not actionable. The CareHub analysis module may analyze performance in real-time, thus providing actionable information at least several months earlier. This enables PCPs to improve their performance. In addition, administrators of the care program (such as FCC) may continuously refine the program to address issues and opportunities to modify patient and PCP behavior; for example, how best to educate and communicate with high-risk patients, and which capacity-building strategies are most effective.

FIG. 24 gives further examples of possible performance measurements and categories. The categories are "Access and Continuity" 2401, "Provider and Patient Engagement" 2402, "Hospital Utilization" 2403, and "Hospital Discharge Management" 2404. It is noteworthy that different measurements are made at different levels of aggregation and frequencies, and with different sources of data.

Another type of possible measurement involves analyzing patient data to determine levels of risk. Once a high-risk patient is identified, specific protocols may be applied to that patient's care; actions in accordance with those protocols may then be tracked, analyzed and rewarded. For example, one patient engagement measurement in FIG. 24 is "percentage of high-risk patient engagement letters signed." This is a valuable measurement, since a signed engagement letter represents the patient's confirmation of the HomePCP relationship. CareHub offers providers the ability to analyze risk factors, assign levels of risk, subsequently define goals and assign activities, and track performance accordingly. It will be appreciated that analyzing and acting on risk, particularly for the purpose of delivering effective care to high-risk patients, is important to the Medical Home concept.

In an additional embodiment, the CareHub may be implemented to facilitate one or more distinct care programs. For example, as shown in FIG. 25, "First Contact for Care" (FCC) is a base program 2501 which involves measurements and rewards limited to shared cost savings in ER utilization and hospital admissions. One or more other programs 2502 may be added to the base program, e.g. to measure performance related to ambulance utilization. CareHub program fees 2503 will typically depend on the type of participant and the scope of the program.

Data-Driven Interactive Learning Environment (DD-ILE)

The Data-Driven Interactive Learning Environment (DD-ILE) module 14 aggregates physicians into peer groups, thereby enabling statistically valid performance assessments combining Utilization data from claims and Service Management data from the CareHub. The DD-ILE enables on-going peer learning with tracking of Plan-Do-Study-Act (PDSA) quality improvement cycles; software tools for Analysis & Visualization, Collaboration, and Social/Professional Networking and effective peer-learning.

The DD-ILE module enables discovery of actionable information; promotes professional networking; facilitates the dissemination of best practices and the privacy and security processes needed for HIPAA. Features of the DD-ILE, in accordance with an embodiment, are as follows:

Enabling discovery of actionable information: DD-ILE aggregates data from fragmented physicians into peer groups—thus enabling statistically valid performance assessments. Furthermore, DD-ILE combines utilization data and new service management data from the point-of-care to give new insight into the changes in care processes that drive measurable outcomes. This combination of data enables various useful assessments, such as measuring patient use of the Medical Home PCP vs. other physicians (see "Performance Measures: ER with CareHub Ticket"). This data is fed into the DD-ILE continuously, thereby enabling continuous quality assessment and continuous peer-induced quality improvement.

Facilitating peer-learning, the dissemination of best practices, and continuous quality improvement: DD-ILE tracks PDSA quality improvement cycles and the effectiveness of specific interventions and presents this information to subsequent users as peer-recommendations and benchmarks. DD- ILE also provides tools for users to create their own PDSAs (e.g. problem, baseline, goals, interventions, progress, results, etc.), thereby further adding to the user-searchable knowledge base of quality improvement processes and their effectiveness in different settings and with different providers and/or patients. DD-ILE provides physicians in small fragmented practices the peer network and part of the infrastructure needed for a virtual Integrated Delivery Network (IDN) or a virtual Accountable Care Organization (ACO). (An advantage of a virtual ACO is that it could be achieved much more readily than could actual legal-financial-physical mergers of small practices into IDNs or large group practices, and thus the benefits of IDNs and ACOs could be realized more rapidly.)

DD-ILE is replicable and financially sustainable: The DD-ILE is tied to payment reform programs—thus helping physicians to earn additional revenues and helping healthcare purchasers (or payers) to save money. DD-ILE is an inexpensive method for remote education/telemedicine that is massively scalable (and becomes more effective with larger scale by aggregating and analyzing more data).

The DD-ILE includes data, tools, and processes needed to discover and act on opportunities for performance improvement, and to measure the improvement, and then disseminate the information. The DD-ILE uses four types of "systemic" (population/network-wide) data: Utilization (from claims); Service Management (from the CareHub); Patient-Reported (from PHRs or surveys), and Clinical (from EMRs via RHIOs) to generate multi-dimensional performance assessments. The DD-ILE includes Analysis and Visualization tools; Online Collaboration tools; Social Networking tools; Content and Curriculum; and the Privacy and Security processes needed for HIPAA compliance and effective peer-learning. Furthermore, DD-ILE may be certified so that physicians can earn Continuing Medical Education (CME) credits.

The DD-ILE aggregates systemic data so that statistically valid analyses can be performed. These analyses are then presented to participating physicians as peer comparisons in order to engender peer-induced performance improvement, thereby making use of the natural dynamic of "doctors learn best from other doctors." The analytic capabilities and peer dynamic are further reinforced with online collaboration and social networking tools, thus giving physicians new access to high-performing role models, and new ways to spread best practices. A "Structured Learning Process", modeled after the Institute for Healthcare Improvement's (IHI) thoroughly tested "Plan-Do-Study-Act" (PDSA) rapid-cycle learning and dissemination model may be embedded in the DD-ILE curriculum.

Individual performance data and system-wide comparisons produced by the DD-ILE are effective to increase transparency and enable value-based purchasing of healthcare services, based on objective measurement of care processes and outcomes. Use of all four types of systemic data enables new multi-dimensional performance assessment and feedback, and the adoption of a "balanced score card" approach to performance improvement. Such objectivity and attributable performance are important to the operation of an Accountable Care Organization, especially those that are made up multiple enterprises.

Incentives for physicians to participate in the DD-ILE are provided by linking the DD-ILE to payment reform programs that provide financial incentives to physicians for improved performance. These incentives give physicians the motivation to improve performance. On-going feeding of the DD-ILE with performance data sustains use of the DD-ILE (i.e. logins to check performance of self and peers), which in turn sustain high performance levels. As the quality improvement objective is achieved in one area, subject areas expand to involve more physicians of different types, further increasing overall relevance and use.

The Data-Driven Interactive Learning Environment (DD-ILE) module 14 aggregates physicians into peer groups, thereby enabling statistically valid performance assessments combining Utilization data from claims and Service Management data from the CareHub. The DD-ILE enables on-going peer learning with tracking of Plan-Do-Study-Act (PDSA) quality improvement cycles; software tools for Analysis & Visualization, Collaboration, and Social/Professional Networking and effective peer-learning.

The DD-ILE module enables discovery of actionable information; promotes professional networking; facilitates the dissemination of best practices and the privacy and security processes needed for HIPAA. Features of the DD-ILE, in accordance with an embodiment, are as follows:

Enabling discovery of actionable information: DD-ILE aggregates data from fragmented physicians into peer groups—thus enabling statistically valid performance assessments. Furthermore, DD-ILE combines utilization data and new service management data from the point-of-care to give new insight into the changes in care processes that drive measurable outcomes. This combination of data enables various useful assessments, such as measuring patient use of the Medical Home PCP vs. other physicians (see "Performance Measures: ER with CareHub Ticket"). This data is fed into the DD-ILE continuously, thereby enabling continuous quality assessment and continuous peer-induced quality improvement.

Facilitating peer-learning, the dissemination of best practices, and continuous quality improvement: DD-ILE tracks PDSA quality improvement cycles and the effectiveness of specific interventions and presents this information to subsequent users as peer-recommendations and benchmarks. DD-ILE also provides tools for users to create their own PDSAs (e.g. problem, baseline, goals, interventions, progress, results, etc.), thereby further adding to the user-searchable knowledge base of quality improvement processes and their effectiveness in different settings and with different providers and/or patients. DD-ILE provides physicians in small fragmented practices the peer network and part of the infrastructure needed for a virtual Integrated Delivery Network (IDN) or a virtual Accountable Care Organization (ACO). (An advantage of a virtual ACO is that it could be achieved much more readily than could actual legal-financial-physical mergers of small practices into IDNs or large group practices, and thus the benefits of IDNs and ACOs could be realized more rapidly.)

DD-ILE is replicable and financially sustainable: The DD-ILE is tied to payment reform programs—thus helping physicians to earn additional revenues and helping healthcare purchasers (or payers) to save money. DD-ILE is an inexpensive method for remote education/telemedicine that is massively scalable (and becomes more effective with larger scale by aggregating and analyzing more data).

The DD-ILE includes data, tools, and processes needed to discover and act on opportunities for performance improvement, and to measure the improvement, and then disseminate the information. The DD-ILE uses four types of "systemic" (population/network-wide) data: Utilization (from claims); Service Management (from the CareHub); Patient-Reported (from PHRs or surveys), and Clinical (from EMRs via RHIOs) to generate multi-dimensional performance assessments. The DD-ILE includes Analysis and Visualization tools; Online Collaboration tools; Social Networking tools; Content and Curriculum; and the Privacy and Security processes needed for HIPAA compliance and effective peer-learning. Furthermore, DD-ILE may be certified so that physicians can earn Continuing Medical Education (CME) credits.

The DD-ILE aggregates systemic data so that statistically valid analyses can be performed. These analyses are then presented to participating physicians as peer comparisons in order to engender peer-induced performance improvement, thereby making use of the natural dynamic of "doctors learn best from other doctors." The analytic capabilities and peer dynamic are further reinforced with online collaboration and social networking tools, thus giving physicians new access to high-performing role models, and new ways to spread best practices. A "Structured Learning Process", modeled after the Institute for Healthcare Improvement's (IHI) thoroughly tested "Plan-Do-Study-Act" (PDSA) rapid-cycle learning and dissemination model may be embedded in the DD-ILE curriculum.

Individual performance data and system-wide comparisons produced by the DD-ILE are effective to increase transparency and enable value-based purchasing of healthcare services, based on objective measurement of care processes and outcomes. Use of all four types of systemic data enables new multi-dimensional performance assessment and feedback, and the adoption of a "balanced score card" approach to performance improvement. Such objectivity and attributable performance are important to the operation of an Accountable Care Organization, especially those that are made up multiple enterprises.

Incentives for physicians to participate in the DD-ILE are provided by linking the DD-ILE to payment reform programs that provide financial incentives to physicians for improved performance. These incentives give physicians the motivation to improve performance. On-going feeding of the DD-ILE with performance data sustains use of the DD-ILE (i.e. logins to check performance of self and peers), which in turn sustain high performance levels. As the quality improvement objective is achieved in one area, subject areas expand to involve more physicians of different types, further increasing overall relevance and use.

Registry

The Registry module 15 tracks patient attributes (disease, condition, age, sex, etc.) and applies diagnosis/treatment/management protocols to those attributes. The module then creates action items and/or reminders for providers and/or patients. Actions taken by providers in response to these items may be tracked, analyzed, and rewarded.

Patient Portal/Public Reporting

The Patient Portal/Public Reporting module 16 is configured to give individual patients access to their data, as well as information on the quality of both payers and providers.

Platform Architecture

The CareHub platform 60 is built in a modular fashion to enable the use of industry standard components from a wide selection of component vendors, and to enable more efficient development, maintenance, and continuous improvement. The CareHub includes all appropriate privacy and security protections, and is HIPAA-compliant.

Figure 26A:
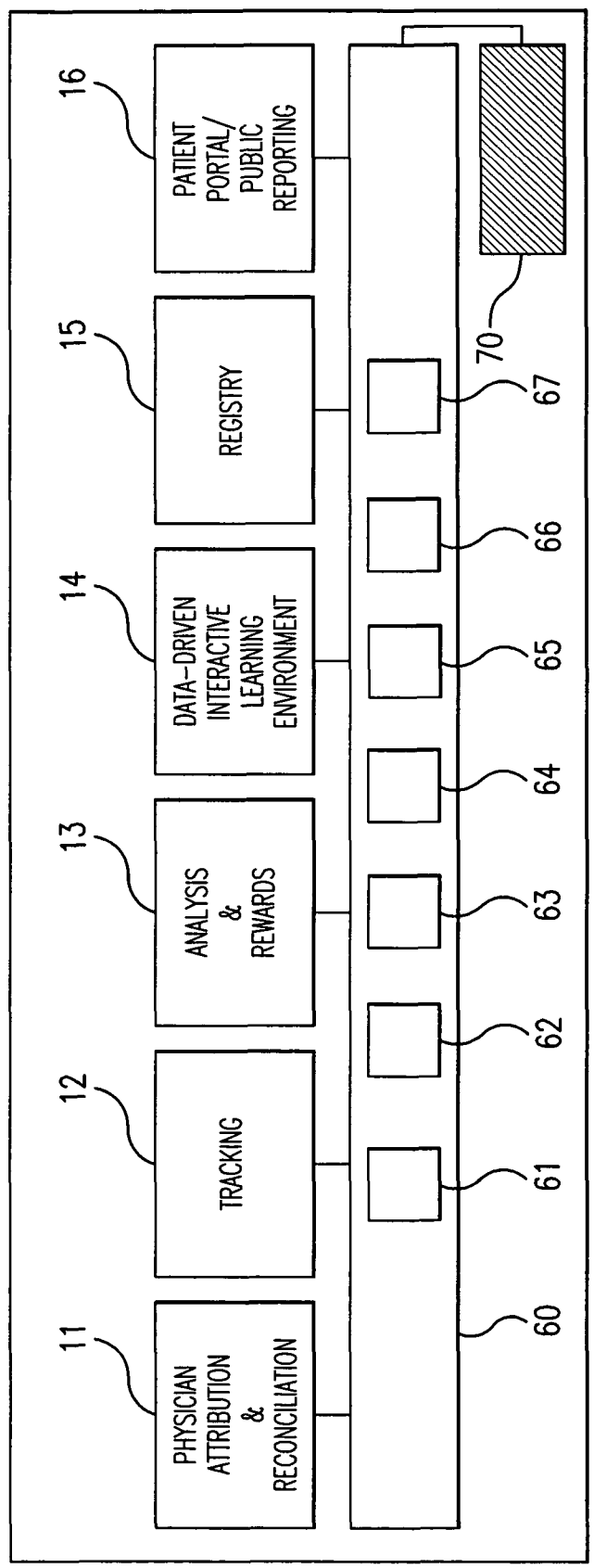
FIGS. 26A and 26B schematically illustrate the architecture of a system, particularly the platform architecture, in an embodiment of the disclosure.

The modules included in platform 60, according to an embodiment of the disclosure, are shown schematically in FIG. 26A.

A Security and Privacy Module 61 implements software mechanisms and rules safeguarding application data from unauthorized disclosure, alteration, loss or destruction. This is accomplished by using Microsoft Windows Server 2008 Active Directory and Identity Lifecycle Manager products.

A Program Configuration and Management Module 62 includes administrative services for processing patient and provider eligibility files and updates sourced from insurers, and managing provider and patient enrollment.

A Shared Patient Profile and Care Plan Module 63 creates and maintains the patient's medical history and a list of the names/practices/specialties of the physicians who have treated the patient. This module provides seamless integration of real-time connections to the insurer's claims system for member medical history, and eligibility system for searches for in-network providers and other benefits information.

A First Contact of Care Module 64 presents the patient's medical history to the PCP (or staff) for use during triage. This module enables PCPs to document triage and referral of patients with urgent needs, including the nature of the needs, and the name of the person responsible for handling the request.

An Access Care Services Module 65 implements tools for creating service requests (e.g. an urgent care need or referral) and matching service requests with qualified providers, with preference given to the patient's care team and in-network providers.

A Work Management Module 66 manages patient and physician requests for service from request through fulfillment. In particular, this module may assign orders to clinical entities and individual providers, place orders on hold awaiting additional information, re-assign orders, change priority and close out orders.

A Service Management Module 67 monitors and measures key performance indicators at the program, process, user, and platform levels. These metrics are used to substantiate adoption, provider performance, value creation and statistical process modeling, optimization and control. This module facilitates physician practices with demand forecasting and cross-entity resource planning, introducing supply chain management concepts and tools to the healthcare delivery system.

Figure 26B:
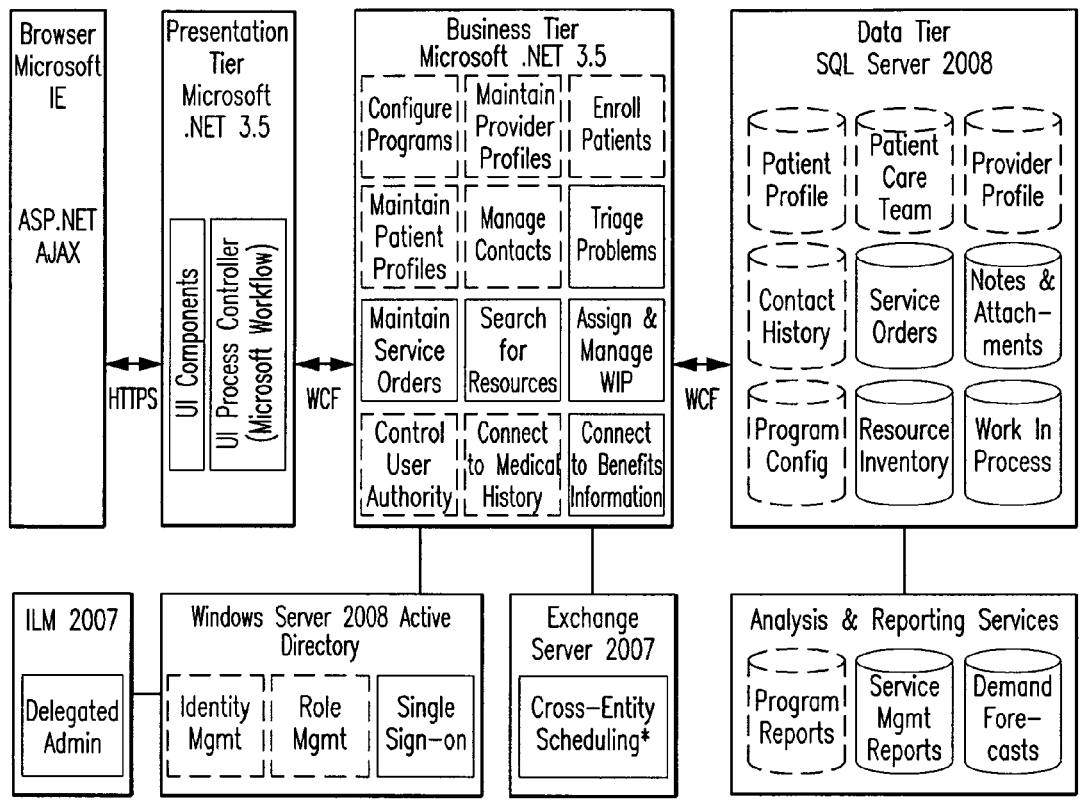

FIG. 26B is a logical-level diagram illustrating the CareHub platform and its underlying technology. In the embodiment shown in FIG. 26B, CareHub has a web-based application architecture based on Microsoft .NET Framework Technologies and SQL Server.

In the embodiment shown in FIG. 26B, Microsoft .NET Framework V3.5 is used to build the Presentation and Business Tiers. The following Microsoft .NET Framework technologies are used in this embodiment:

Windows Communication Foundation (WCF) provides a unified framework for rapidly building high-performance service-oriented applications, facilitating secure and reliable Web services.

Windows Workflow Foundation (WF) provides a programming model, engine and tools for quickly building workflow-enabled applications on Windows. WF supports both system workflow and human workflow.

Base Class Libraries (BCL) provides fundamental building blocks for applications.

ASP.NET, a version of Active Server Pages (ASP), is a programming framework used to build enterprise-class Web user interfaces. ASP.NET uses the Common Language Runtime, provided by the .NET Framework, to manage execution of the code. ASP.NET includes support for AJAX, a collection of standards-based JavaScript classes that permit user interfaces to be rendered dynamically in a Web browser without requiring interaction with the Web server.

ADO.NET provides a set of data access services to .NET programmers for connecting applications to data sources such as Microsoft SQL Server and XML.

Common Language Runtime (CLR) is the .NET Framework run-time environment.

SQL Server is used to implement the Analysis & Reporting Services and Data Tier. SQL Server supports the storage and management of data in multiple formats within a database, including relational data, XML files and unstructured documents, such as scanned images. SQL Server delivers a set of integrated services to query, search, synchronize, report and analyze data.

Mobile Access

CareHub-MobileAccess (CH-MA) is a mobile-phone version of the CareHub which permits PCPs to document access to care without having to return to a desktop computer. It will be appreciated that the mobility and ubiquity afforded by mobile phones helps to improve response times to urgent call requests, and also improves the timeliness and accuracy of the documentation of access to care and coordination of care. CH-MA is especially effective after working hours, when PCPs are away from their offices (and computers) and when "on-call" or cross-covering for other PCPs. Effective management of access to care and coordination of care in these situations is particularly important, as a substantial proportion of avoidable hospital utilization takes place during these times.

Figure 27:
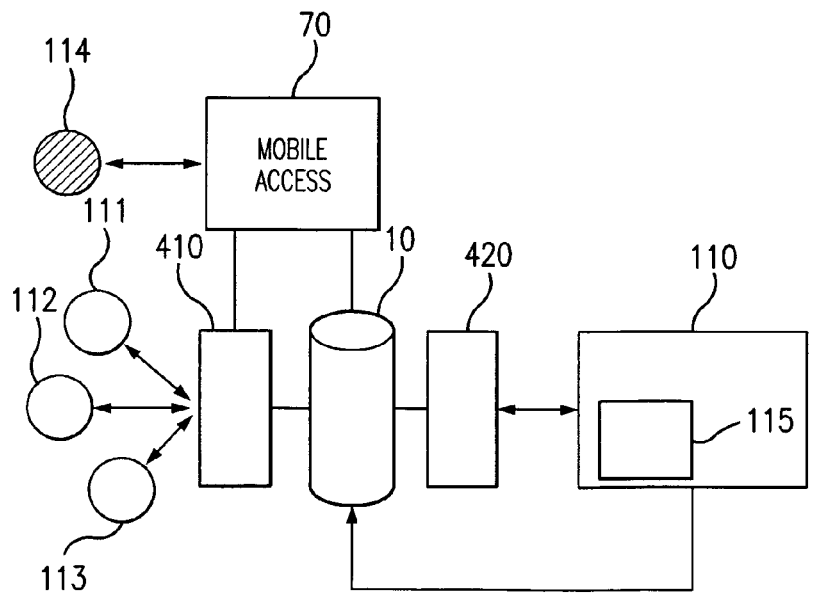
FIG. 27 schematically illustrates a mobile access module used in a system embodying the disclosure.

As shown schematically in FIG. 26A, the CH-MA software 70 is a mobile extension of the CareHub platform, as opposed to a mobile-only application. As shown in FIG. 27, a user 114 (e.g. a PCP with an iPad, iPhone or similar device) may access all of the features of the CareHub system using the CH-MA software.

While the disclosure has been described in terms of specific embodiments, it is evident in view of the foregoing description that numerous alternatives, modifications and variations will be apparent to those skilled in the art. Accordingly, the disclosure is intended to encompass all such alternatives, modifications and variations which fall within the scope and spirit of the disclosure and the following claims.

What is claimed is:

1. A method, for execution on a computing device, comprising:
    accessing, by a computing device, clinical data and medical claims data relating to care for a group of patients;
    by a computing device, establishing relationships between patients and providers, said patients being on a list of eligible patients and said providers being in a directory of providers, including attributing a patient to a provider in accordance with at least one of the medical claims data and a predetermined rule, wherein said step of establishing relationships includes:
        determining from the medical claims data whether a patient may be attributed to one provider only, to a plurality of providers, or to no provider;
    where the patient may be attributed to one provider only, attributing the patient to that provider, requesting confirmation of a patient-to-provider (P2P) relationship from the provider, and receiving communication from the provider regarding acceptance of the P2P relationship,
        where the patient may be attributed to a plurality of providers, attributing the patient to each of said plurality of providers, requesting confirmation of a P2P relationship from each of said plurality of providers, and receiving communication from at least of said plurality of providers regarding acceptance of the P2P relationship, and where the patient may be attributed to no provider, attributing the patient to a provider in the directory of providers in accordance with a first rule;
    requesting confirmation from said provider regarding a patient-provider relationship with said patient; and
    recording clinical events related to an urgent care request, said events including an initial communication requesting care, and fulfillment of the request; and
    by a computing device, measuring performance of the provider of said care with respect to at least one predetermined criterion.

2. A method according to claim 1, wherein the claims data, the patient eligibility list, and the provider directory are maintained by a payer entity.

3. A method according to claim 2, wherein said determining is performed in accordance with treatment codes associated with care delivered to the patient by a given provider.

4. A method according to claim 3, wherein said determining is performed in accordance with evaluation and management (E&M) codes associated with care delivered to the patient by a given primary care provider.

5. A method according to claim 2, further including
    where provider communication indicates acceptance of a P2P relationship with a patient by a plurality of providers,
        performing a reconciliation process to attribute the patient to one of said plurality of providers; and
    where provider communication indicates acceptance of a P2P relationship with a patient by no providers,
        attributing the patient to a provider in the director of providers in accordance with a second rule,
    wherein the first rule and the second rule are determined by the payer entity.

6. A method according to claim 5, wherein said reconciliation process further includes
    requesting further communication regarding the P2P relationship from at least one of
        a provider in the directory of providers,
        a committee of predetermined membership,
        a representative of the payer entity, and
        the patient,
    wherein said reconciliation process is performed according to user-configurable rules.

7. A method according to claim 1, further comprising
    providing a user interface for performing said requesting and said recording; and
    displaying information regarding said relationships and results of said measuring via said user interface.

8. A method according to claim 1, wherein said recording step further includes
    recording triage of the request,
    recording assessment of the request, said assessment including a working diagnosis, and
    recording assignment of the request to a provider responsible for delivering said care.

9. A method according to claim 8, further comprising
    displaying a status of a pending urgent care request;
    displaying a list of requests awaiting at least one of assessment and assignment, the list including an elapsed time since recording of the initial communication requesting care.

10. A method according to claim 9, further comprising
    displaying a list of requests indicating that
        a hospital discharge is pending, wherein a patient has been admitted to a hospital, or
        a hospital discharge has occurred, wherein a patient has been discharged from a hospital.

11. A method according to claim 8, wherein a pending urgent care request is characterized as an open ticket, the ticket being opened on recording of the initial communication requesting care and closed on recording of fulfillment of the request.

12. A method according to claim 1, wherein fulfillment of the request is recorded in accordance with one of
delivery of care by a provider in the directory of providers, said delivery being documented via a user interface, and
delivery of care by a provider not in the directory of providers, said delivery being documented on the basis of the medical claims data.

13. A method according to claim 1, wherein said measuring step further includes
determining a formula for measuring performance with respect to the criterion;
calculating a baseline performance in accordance with said formula;
calculating a performance result in accordance with said formula;
calculating a change in performance with respect to said baseline performance; and
displaying a report including at least one of the performance result and the change in performance.

14. A method according to claim 13, wherein performance of a plurality of providers is measured, and said report includes a range of performance results.

15. A method according to claim 14, wherein
an improvement in performance is characterized as a change in an average value of said performance results, and
said improvement is measured with respect to a range of improvement, the range of improvement having a low level corresponding to the lowest value of the performance results, and a high level corresponding to one of the highest value of the performance results and a value in accordance with published best practices.

16. A method according to claim 13, further comprising:
identifying a high-risk patient in accordance with the patient's expected need for care; and
determining an action for performance by a provider having a P2P relationship with said high-risk patient,
and wherein said measuring step further includes measuring performance of said provider with respect to said action.

17. A method according to claim 1, further comprising:
accessing cost data relating to a health care program;
determining, in accordance with said cost data, a net cost savings for the program over a predetermined period of time;
calculating shares of said net cost savings at least partially in accordance with said performance; and
distributing a share of said net cost savings to the provider.

18. A method according to claim 17, further comprising:
determining an improvement in performance from a comparison of said performance with one of
a baseline performance and
a performance during a specified previous time period,
and wherein said calculating step further includes
calculating a relative weight of said performance and said improvement; and
calculating the shares in accordance with said performance, said improvement, and the relative weight.

19. A method according to claim 17, further comprising:
where a given provider belongs to a group of providers, measuring performance of the individual provider and of the group,
and wherein said calculating step further includes
calculating a relative weight of individual performance and group performance; and
calculating the shares in accordance with the individual performance, the group performance, and the relative weight.

20. A method according to claim 17, wherein said calculating step further includes
determining a patient panel weight factor for the provider in accordance with a number of patient months for the provider; and
calculating the shares in accordance with the patient panel weight factor.

21. A method according to claim 1, further comprising:
formulating a Plan-Do-Study-Act (PDSA) quality improvement cycle for a provider; and
tracking the performance of the provider with reference to the PDSA quality improvement cycle.

22. A method according to claim 21, further comprising:
tracking effectiveness of specific interventions regarding patient care; and
presenting information regarding said tracking to users of the method as peer-recommendations and/or benchmarks.

23. A method according to claim 22, further comprising
displaying information regarding recommended performance improvements and/or treatment protocols.

24. A method according to claim 21, wherein said tracking includes tracking performance of a plurality of providers, and further comprising
presenting peer-to-peer comparisons of performance.

25. A method according to claim 1, wherein said method is performed using web-based software delivered to users' computing devices via a network.

26. A method according to claim 25, wherein said software is configured as a plurality of modules.

27. A method according to claim 25, wherein said software is configured for access by a user's mobile computing device.

* * * * *